US011382908B2

(12) United States Patent
Leshchiner et al.

(10) Patent No.: US 11,382,908 B2
(45) Date of Patent: Jul. 12, 2022

(54) COMPOSITIONS AND METHODS FOR TREATING INFLAMMATORY BOWEL DISEASE

(71) Applicants: The Broad Institute, Inc., Cambridge, MA (US); The General Hospital Corporation, Boston, MA (US); President and Fellows of Harvard College, Cambridge, MA (US)

(72) Inventors: Elizaveta Leshchiner, Cambridge, MA (US); Zhifang Cao, Cambridge, MA (US); Jason Rush, Cambridge, MA (US); Michael Durney, Cambridge, MA (US); Alykhan Shamji, Cambridge, MA (US); Daniel Graham, Cambridge, MA (US); Stuart L. Schreiber, Cambridge, MA (US); Ramnik Xavier, Cambridge, MA (US)

(73) Assignees: The Broad Institute, Inc., Cambridge, MA (US); The General Hospital Corporation, Boston, MA (US); President and Fellows of Harvard College, Cambridge, MA (US)

( * ) Notice: Subject to any disclaimer, the term of this patent is extended or adjusted under 35 U.S.C. 154(b) by 55 days.

(21) Appl. No.: 16/651,163

(22) PCT Filed: Sep. 26, 2018

(86) PCT No.: PCT/US2018/052845
§ 371 (c)(1),
(2) Date: Mar. 26, 2020

(87) PCT Pub. No.: WO2019/067530
PCT Pub. Date: Apr. 4, 2019

(65) Prior Publication Data
US 2020/0268736 A1    Aug. 27, 2020

Related U.S. Application Data

(60) Provisional application No. 62/563,381, filed on Sep. 26, 2017.

(51) Int. Cl.
*A61K 31/4545*    (2006.01)
*A61K 31/496*    (2006.01)

(52) U.S. Cl.
CPC ........ *A61K 31/4545* (2013.01); *A61K 31/496* (2013.01)

(58) Field of Classification Search
CPC ..... A61K 31/4545; A61K 31/496; A61P 1/00; A61P 1/04; A61P 29/00; A61P 43/00
See application file for complete search history.

(56) References Cited

U.S. PATENT DOCUMENTS

2012/0107317 A1* 5/2012 Lau .................... A61P 37/06
424/138.1

FOREIGN PATENT DOCUMENTS

| EP | 1176140 A1 | 1/2002 |
| EP | 1391199 A1 | 2/2004 |
| EP | 1775298 A1 | 4/2007 |
| WO | WO-2011/048004 A1 | 4/2011 |
| WO | WO-2011/140190 A1 | 11/2011 |
| WO | WO-2014/055634 A1 | 4/2014 |
| WO | WO-2014071247 A1 * | 5/2014 ........... C07D 409/04 |

OTHER PUBLICATIONS

PubChem, CID 880567, publ. Jul. 9, 2005 (Year: 2005).*
Cao et al., "The ubiquitin ligase TRIM62 regulates CARD9-mediated anti-fungal immunity and intestinal inflammation," Immunity, 715-726 (2015).
International Search Report and Written Opinion for International Application No. PCT/US2018/052845 dated Dec. 26, 2018.
Leshchiner et al., "Small-molecule inhibitors directly target CARD9 and mimic its protective variant in inflammatory bowel disease," PNAS, 114(43):11392-11397 (2017).
PubChem AID 504339, "qHTS Assay for Inhibitors of JMJD2A-Tudor Domain," (2011).

* cited by examiner

*Primary Examiner* — Sarah Pihonak
(74) *Attorney, Agent, or Firm* — Foley Hoag LLP; David P. Halstead

(57) ABSTRACT

Disclosed herein are compounds for the treatment of inflammatory bowel disease. Additionally, provided herein are compositions and methods for using these compounds and compositions in the treatment of inflammatory bowel disease in a subject.

20 Claims, 12 Drawing Sheets

Compound 7

Compound 27

Truhit control kit

* Compound 9
* Compound 6
* Compound 7
* Compound 27

Compound 11

| 1 | CARD9 + TRIM62 | 13 | Compound 16 |
| 2 | CARD9 + TRIM62 + CTD | 14 | Compound 17 |
| 3 | Compound 9 | 15 | Compound 18 |
| 4 | Compound 6 | 16 | Compound 19 |
| 5 | Compound 10 | 17 | Compound 20 |
| 6 | Compound 27 | 18 | Compound 21 |
| 7 | Compound 8 | 19 | Compound 22 |
| 8 | Compound 2 | 20 | Compound 23 |
| 9 | Compound 12 | 21 | Compound 24 |
| 10 | Compound 13 | 22 | Compound 25 |
| 11 | Compound 14 | 23 | Compound 26 |
| 12 | Compound 5 | | |

FIG. 6

| Compound | Activity in CARD9-TRIM62 disruption | Activity in CARD9 Ubiquitination disruption |
|---|---|---|
| 2 | 22.3 µM | 35.8 µM |
| 27 | 6.0 µM | 18.2 µM |
| 9 | 8.6 µM | 9.2 µM |
| 4 | 18.2 µM | ~40 µM |
| 5 | 45.1 µM | >40 µM |
| 6 | 3.2 µM | 6.6 µM |

FIG. 6 (cont.)

| Compound | Activity in CARD9-TRIM62 disruption | Activity in CARD9 Ubiquitination disruption |
|---|---|---|
| 7 | 6.6 μM | 14.2 μM |
| 8 | 7.4 μM | 9.0 μM |
| 3 | 22.0 μM | Not disclosed |
| 10 | 14.4 μM | Not disclosed |
| 11 | 40.7 μM | Not disclosed |

COMPOSITIONS AND METHODS FOR TREATING INFLAMMATORY BOWEL DISEASE

RELATED APPLICATIONS

This application is the U.S. national phase of International Patent Application No. PCT/US2018/052845, filed Sep. 26, 20186, which claims the benefit of U.S. Provisional Application No. 62/563,381 filed on Sep. 26, 2017, which are hereby incorporated by reference in their entirety.

BACKGROUND

Inflammatory bowel disease (IBD) is a group of autoimmune inflammatory conditions of the colon and small intestine, which means the patient's immune system attacks areas of the digestive system. Crohn's disease and ulcerative colitis are the principal types of inflammatory bowel disease. Inflammatory bowel disease affects over 1 million people in the United States alone. Genetic studies, such as genome-wide association (GWAS), on the risk of developing inflammatory bowel disease has identified genes that may correlate with developing the disease. These genes included ones related with cytokine production, lymphocyte activation and the response to bacterial infection.

For example, CARD9 is a member of the CARD protein family, which is defined by the presence of a characteristic caspase-associated recruitment domain (CARD). CARD is a protein interaction domain known to participate in activation or suppression of CARD containing members of the caspase family. In exome-sequencing studies, CARD9 variants were shown to have significant risk as well as protective associations with IBD[2,5]. CARD9 plays a key role in mediating innate immune signaling from C-type-Lectin receptors (CLRs), such as Dectin-1 and Mincle, which are responsible for recognition of fungi and mycobacteria in myeloid cells and dendritic cells. A protective variant of CARD9, CARD9Δ11, has been described as reducing the risk of contracting IBD (Cao, Z. et al. Ubiquitin Ligase TRIM62 Regulates CARD9-Mediated Anti-fungal Immunity and Intestinal Inflammation. *Immunity* 43, 715-726).

However, these genetic studies have yet to translate into any small molecule IBD therapeutic or prophylactic for patients. Therefore, the creation of selective CARD9 modulators could lead to a new class of IBD therapy.

SUMMARY

Provided herein is a method of treating inflammatory bowel disease, comprising administering to a subject a compound of Formula I or a pharmaceutically acceptable salt thereof:

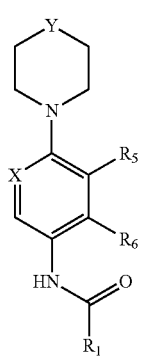

I wherein:
X is N or CH;
Y is $NR_2$ or $CR_3R_4$;
$R_1$ is selected from alkyl, cycloalkyl, aryl and heteroaryl;
$R_2$ is selected from acyl, aryl, and heteroaryl;
$R_3$ is selected from H, alkyl, and heterocyclyl;
$R_4$ is selected from H, alkyl and amido; and
one of $R_5$ and $R_6$ is —COOH and the other is H.

Also provided herein is a method of modulating CARD9, comprising administering to a subject a compound of Formula I or a pharmaceutically acceptable salt thereof:

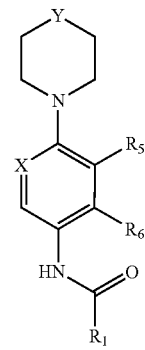

I wherein:
X is N or CH;
Y is $NR_2$ or $CR_3R_4$;
$R_1$ is selected from alkyl, cycloalkyl, aryl and heteroaryl;
$R_2$ is selected from acyl, aryl, and heteroaryl;
$R_3$ is selected from H, alkyl, and heterocyclyl;
$R_4$ is selected from H, alkyl and amido; and
one of $R_5$ and $R_6$ is —COOH and the other is H.

Disclosed herein are compounds of Formula I, or a pharmaceutically acceptable salt thereof:

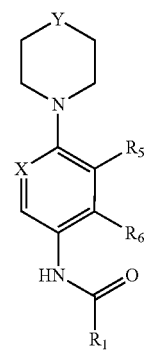

I wherein:
X is N or CH;
Y is $NR_2$ or $CR_3R_4$;
$R_1$ is selected from alkyl, cycloalkyl, aryl and heteroaryl;
$R_2$ is selected from acyl, aryl, and heteroaryl;
$R_3$ is selected from H, alkyl, and heterocyclyl;
$R_4$ is selected from H, alkyl and amido; and
one of $R_5$ and $R_6$ is —COOH and the other is H.

BRIEF DESCRIPTION OF THE DRAWINGS

FIG. 6 provides data for compounds of the invention in both the Luminex and AlphaLISA ubiquitinylation assays, demonstrating their ability to inhibit the interaction of CARD9 and TRIM62 and prevent CARD9 ubiquitinylation.

DESCRIPTION

Definitions

Figure 1A:
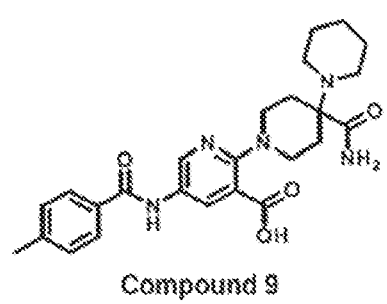
FIG. 1 indicates that compounds 9 (FIG. 1A), 6 (FIG. 1B), 7 (FIG. 1C), and 27 (FIG. 1D) are dose-dependent inhibitors in a CARD9-TRIM62 protein-protein interaction assay.
Figure 1A:
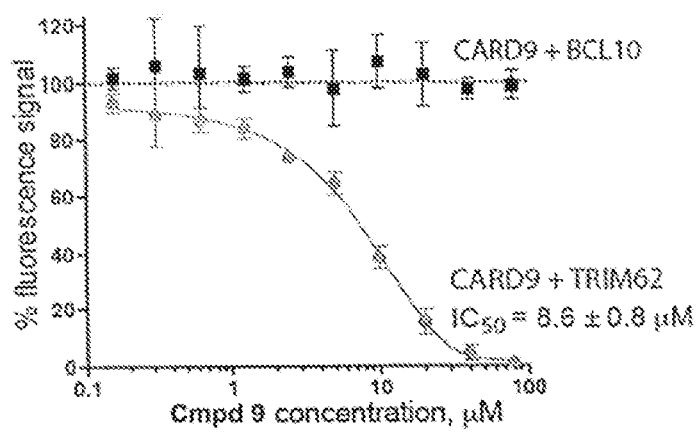
Figure 1B:
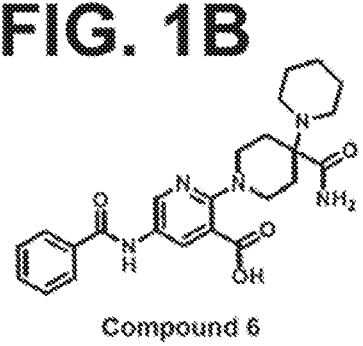
Figure 1B:
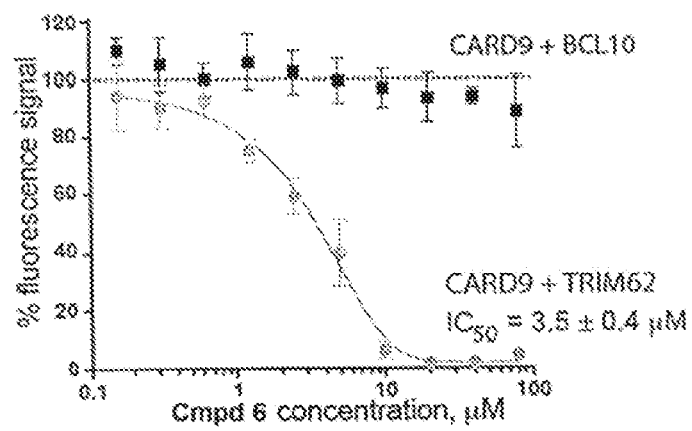
Figure 1C:
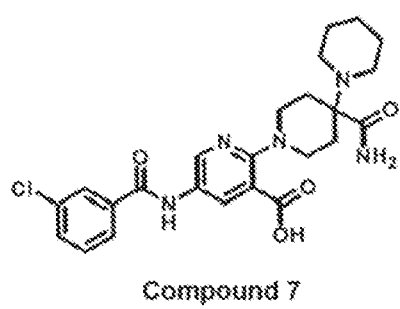
Figure 1C:
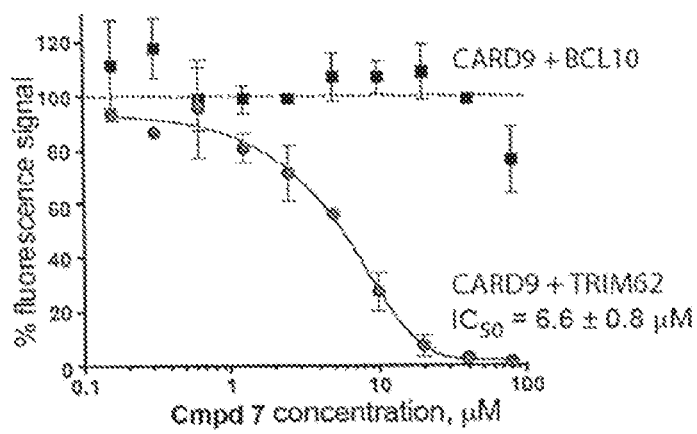
Figure 1D:
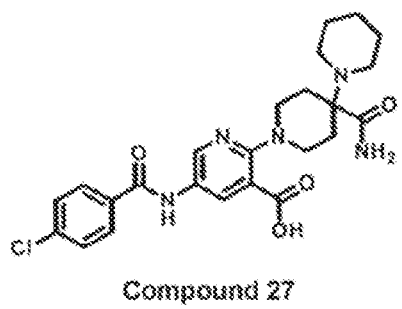
Figure 1D:
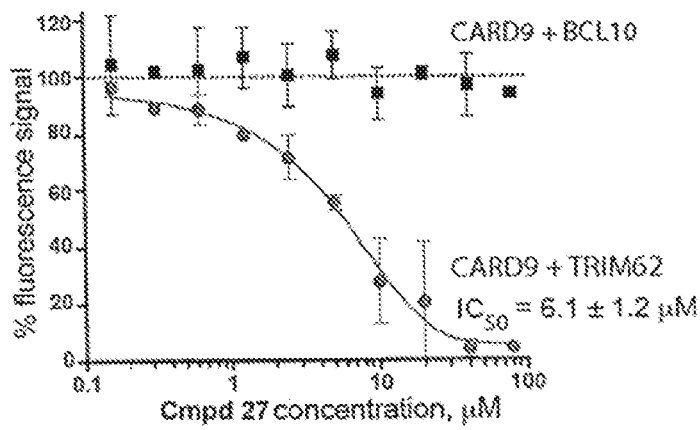

The term "acyl" is art-recognized and refers to a group represented by the general formula hydrocarbylC(O)—, preferably alkylC(O)—.

The term "acylamino" is art-recognized and refers to an amino group substituted with an acyl group and may be represented, for example, by the formula hydrocarbylC(O)NH—.

The term "acyloxy" is art-recognized and refers to a group represented by the general formula hydrocarbylC(O)O—, preferably alkylC(O)O—.

The term "alkoxy" refers to an alkyl group, preferably a lower alkyl group, having an oxygen attached thereto. Representative alkoxy groups include methoxy, ethoxy, propoxy, tert-butoxy and the like.

The term "alkoxyalkyl" refers to an alkyl group substituted with an alkoxy group and may be represented by the general formula alkyl-O-alkyl.

The term "alkenyl", as used herein, refers to an aliphatic group containing at least one double bond and is intended to include both "unsubstituted alkenyls" and "substituted alkenyls", the latter of which refers to alkenyl moieties having substituents replacing a hydrogen on one or more carbons of the alkenyl group. Such substituents may occur on one or more carbons that are included or not included in one or more double bonds. Moreover, such substituents include all those contemplated for alkyl groups, as discussed below, except where stability is prohibitive. For example, substitution of alkenyl groups by one or more alkyl, carbocyclyl, aryl, heterocyclyl, or heteroaryl groups is contemplated.

An "alkyl" group or "alkane" is a straight chained or branched non-aromatic hydrocarbon which is completely saturated. Typically, a straight chained or branched alkyl group has from 1 to about 20 carbon atoms, preferably from 1 to about 10 unless otherwise defined. Examples of straight chained and branched alkyl groups include methyl, ethyl, n-propyl, iso-propyl, n-butyl, sec-butyl, tert-butyl, pentyl, hexyl, pentyl and octyl. A $C_1$-$C_6$ straight chained or branched alkyl group is also referred to as a "lower alkyl" group.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. Such substituents, if not otherwise specified, can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, alkylthios, aminoalkyls, carbonyl-substituted alkyls, —$CF_3$, —CN, and the like.

The term "$C_{x-y}$" when used in conjunction with a chemical moiety, such as, acyl, acyloxy, alkyl, alkenyl, alkynyl, or alkoxy is meant to include groups that contain from x to y carbons in the chain. For example, the term "$C_{x-y}$alkyl" refers to substituted or unsubstituted saturated hydrocarbon groups, including straight-chain alkyl and branched-chain alkyl groups that contain from x to y carbons in the chain, including haloalkyl groups such as trifluoromethyl and 2,2, 2-trifluoroethyl, etc. $C_0$ alkyl indicates a hydrogen where the group is in a terminal position, a bond if internal. The terms "$C_{2-y}$alkenyl" and "$C_{2-y}$alkynyl" refer to substituted or unsubstituted unsaturated aliphatic groups analogous in length and possible substitution to the alkyls described above, but that contain at least one double or triple bond respectively.

The term "alkylamino", as used herein, refers to an amino group substituted with at least one alkyl group.

The term "alkylthio", as used herein, refers to a thiol group substituted with an alkyl group and may be represented by the general formula alkylS—.

The term "alkynyl", as used herein, refers to an aliphatic group containing at least one triple bond and is intended to include both "unsubstituted alkynyls" and "substituted alkynyls", the latter of which refers to alkynyl moieties having substituents replacing a hydrogen on one or more carbons of the alkynyl group. Such substituents may occur on one or more carbons that are included or not included in one or more triple bonds. Moreover, such substituents include all those contemplated for alkyl groups, as discussed above, except where stability is prohibitive. For example, substitution of alkynyl groups by one or more alkyl, carbocyclyl, aryl, heterocyclyl, or heteroaryl groups is contemplated.

The term "amide", as used herein, refers to a group

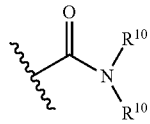

wherein each $R^{10}$ independently represents a hydrogen or hydrocarbyl group, or two $R^{10}$ are taken together with the N atom to which they are attached complete a heterocycle having from 4 to 8 atoms in the ring structure.

The terms "amine" and "amino" are art-recognized and refer to both unsubstituted and substituted amines and salts thereof, e.g., a moiety that can be represented by

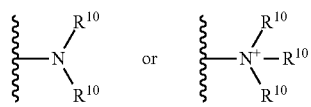

wherein each $R^{10}$ independently represents a hydrogen or a hydrocarbyl group, or two $R^{10}$ are taken together with the N atom to which they are attached complete a heterocycle having from 4 to 8 atoms in the ring structure. The term "aminoalkyl", as used herein, refers to an alkyl group substituted with an amino group.

The term "aralkyl", as used herein, refers to an alkyl group substituted with an aryl group.

The term "aryl" as used herein include substituted or unsubstituted single-ring aromatic groups in which each atom of the ring is carbon. Preferably, the ring is a 5- to 7-membered ring, more preferably a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The term "carbamate" is art-recognized and refers to a group

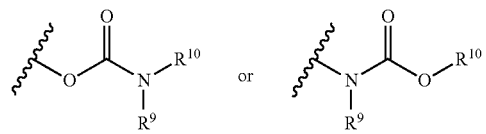

wherein $R^9$ and $R^{10}$ independently represent hydrogen or a hydrocarbyl group, such as an alkyl group, or $R^9$ and $R^{10}$ taken together with the intervening atom(s) complete a heterocycle having from 4 to 8 atoms in the ring structure.

The terms "carbocycle", and "carbocyclic", as used herein, refers to a saturated or unsaturated ring in which each atom of the ring is carbon. The term carbocycle includes both aromatic carbocycles and non-aromatic carbocycles. Non-aromatic carbocycles include both cycloalkane rings, in which all carbon atoms are saturated, and cycloalkene rings, which contain at least one double bond.

The term "carbocycle" includes 5-7 membered monocyclic and 8-12 membered bicyclic rings. Each ring of a bicyclic carbocycle may be selected from saturated, unsaturated and aromatic rings. Carbocycle includes bicyclic molecules in which one, two or three or more atoms are shared between the two rings. The term "fused carbocycle" refers to a bicyclic carbocycle in which each of the rings shares two adjacent atoms with the other ring. Each ring of a fused carbocycle may be selected from saturated, unsaturated and aromatic rings. In an exemplary embodiment, an aromatic ring, e.g., phenyl, may be fused to a saturated or unsaturated ring, e.g., cyclohexane, cyclopentane, or cyclohexene. Any combination of saturated, unsaturated and aromatic bicyclic rings, as valence permits, is included in the definition of carbocyclic. Exemplary "carbocycles" include cyclopentane, cyclohexane, bicyclo[2.2.1]heptane, 1,5-cyclooctadiene, 1,2,3,4-tetrahydronaphthalene, bicyclo[4.2.0]oct-3-ene, naphthalene and adamantane. Exemplary fused carbocycles include decalin, naphthalene, 1,2,3,4-tetrahydronaphthalene, bicyclo[4.2.0]octane, 4,5,6,7-tetrahydro-1H-indene and bicyclo[4.1.0]hept-3-ene. "Carbocycles" may be susbstituted at any one or more positions capable of bearing a hydrogen atom.

A "cycloalkyl" group is a cyclic hydrocarbon which is completely saturated. "Cycloalkyl" includes monocyclic and bicyclic rings. Typically, a monocyclic cycloalkyl group has from 3 to about 10 carbon atoms, more typically 3 to 8 carbon atoms unless otherwise defined. The second ring of a bicyclic cycloalkyl may be selected from saturated, unsaturated and aromatic rings. Cycloalkyl includes bicyclic molecules in which one, two or three or more atoms are shared between the two rings. The term "fused cycloalkyl" refers to a bicyclic cycloalkyl in which each of the rings shares two adjacent atoms with the other ring. The second ring of a fused bicyclic cycloalkyl may be selected from saturated, unsaturated and aromatic rings. A "cycloalkenyl" group is a cyclic hydrocarbon containing one or more double bonds.

The term "carbocyclylalkyl", as used herein, refers to an alkyl group substituted with a carbocycle group.

The term "carbonate" is art-recognized and refers to a group —OCO$_2$—R$^{10}$, wherein R$^{10}$ represents a hydrocarbyl group.

The term "carboxy", as used herein, refers to a group represented by the formula —CO$_2$H.

The term "ester", as used herein, refers to a group —C(O)OR$^{10}$ wherein R$^{10}$ represents a hydrocarbyl group.

The term "ether", as used herein, refers to a hydrocarbyl group linked through an oxygen to another hydrocarbyl group. Accordingly, an ether substituent of a hydrocarbyl group may be hydrocarbyl-O—. Ethers may be either symmetrical or unsymmetrical. Examples of ethers include, but are not limited to, heterocycle-O-heterocycle and aryl-O-heterocycle. Ethers include "alkoxyalkyl" groups, which may be represented by the general formula alkyl-O-alkyl.

The terms "halo" and "halogen" as used herein means halogen and includes chloro, fluoro, bromo, and iodo.

The terms "hetaralkyl" and "heteroaralkyl", as used herein, refers to an alkyl group substituted with a hetaryl group.

The term "heteroalkyl", as used herein, refers to a saturated or unsaturated chain of carbon atoms and at least one heteroatom, wherein no two heteroatoms are adjacent.

The terms "heteroaryl" and "hetaryl" include substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The terms "heteroaryl" and "hetaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, and pyrimidine, and the like.

The term "heteroatom" as used herein means an atom of any element other than carbon or hydrogen. Preferred heteroatoms are nitrogen, oxygen, and sulfur.

The terms "heterocyclyl", "heterocycle", and "heterocyclic" refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. The terms "heterocyclyl" and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, morpholine, lactones, lactams, and the like.

The term "heterocyclylalkyl", as used herein, refers to an alkyl group substituted with a heterocycle group.

The term "hydrocarbyl", as used herein, refers to a group that is bonded through a carbon atom that does not have a =O or =S substituent, and typically has at least one carbon-hydrogen bond and a primarily carbon backbone, but may optionally include heteroatoms. Thus, groups like methyl, ethoxyethyl, 2-pyridyl, and trifluoromethyl are considered to be hydrocarbyl for the purposes of this application, but substituents such as acetyl (which has a =O substituent on the linking carbon) and ethoxy (which is linked through oxygen, not carbon) are not. Hydrocarbyl groups include, but are not limited to, aryl, heteroaryl, carbocycle, heterocyclyl, alkyl, alkenyl, alkynyl, and combinations thereof.

The term "hydroxyalkyl", as used herein, refers to an alkyl group substituted with a hydroxy group.

The term "lower" when used in conjunction with a chemical moiety, such as, acyl, acyloxy, alkyl, alkenyl, alkynyl, or alkoxy is meant to include groups where there are ten or fewer non-hydrogen atoms in the substituent, preferably six or fewer. A "lower alkyl", for example, refers to an alkyl group that contains ten or fewer carbon atoms, preferably six or fewer. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

The terms "polycyclyl", "polycycle", and "polycyclic" refer to two or more rings (e.g., cycloalkyls, cycloalkenyls, cycloalkynyls, aryls, heteroaryls, and/or heterocyclyls) in which two or more atoms are common to two adjoining rings, e.g., the rings are "fused rings". Each of the rings of the polycycle can be substituted or unsubstituted. In certain embodiments, each ring of the polycycle contains from 3 to 10 atoms in the ring, preferably from 5 to 7.

The term "silyl" refers to a silicon moiety with three hydrocarbyl moieties attached thereto.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that substituents can themselves be substituted, if appropriate. Unless specifically stated as "unsubstituted," references to chemical moieties herein are understood to include substituted variants. For example, reference to an "aryl" group or moiety implicitly includes both substituted and unsubstituted variants.

The term "sulfate" is art-recognized and refers to the group —OSO$_3$H, or a pharmaceutically acceptable salt thereof.

The term "sulfonamide" is art-recognized and refers to the group represented by the general formulae

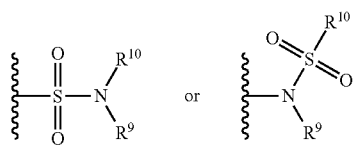

wherein R$^9$ and R$^{10}$ independently represents hydrogen or hydrocarbyl, such as alkyl, or R$^9$ and R$^{10}$ taken together with the intervening atom(s) complete a heterocycle having from 4 to 8 atoms in the ring structure.

The term "sulfoxide" is art-recognized and refers to the group —S(O)—R$^{10}$, wherein R$^{10}$ represents a hydrocarbyl.

The term "sulfonate" is art-recognized and refers to the group SO$_3$H, or a pharmaceutically acceptable salt thereof.

The term "sulfone" is art-recognized and refers to the group —S(O)$_2$—R$^{10}$, wherein R$^{10}$ represents a hydrocarbyl.

The term "thioalkyl", as used herein, refers to an alkyl group substituted with a thiol group.

The term "thioester", as used herein, refers to a group —C(O)SR$^{10}$ or —SC(O)R$^{10}$ wherein R$^{10}$ represents a hydrocarbyl.

The term "thioether", as used herein, is equivalent to an ether, wherein the oxygen is replaced with a sulfur.

The term "urea" is art-recognized and may be represented by the general formula

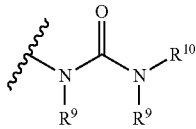

wherein R$^9$ and R$^{10}$ independently represent hydrogen or a hydrocarbyl, such as alkyl, or either occurrence of R$^9$ taken together with R$^{10}$ and the intervening atom(s) complete a heterocycle having from 4 to 8 atoms in the ring structure.

The term "protecting group" refers to a group of atoms that, when attached to a reactive functional group in a molecule, mask, reduce or prevent the reactivity of the functional group. Typically, a protecting group may be selectively removed as desired during the course of a synthesis. Examples of protecting groups can be found in Greene and Wuts, *Protective Groups in Organic Chemistry*, 3$^{rd}$ Ed., 1999, John Wiley & Sons, NY and Harrison et al., *Compendium of Synthetic Organic Methods*, Vols. 1-8, 1971-1996, John Wiley & Sons, NY. Representative nitrogen protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("TES"), trityl and substituted trityl groups, allyloxycarbonyl, 9-fluorenylmethyloxycarbonyl ("FMOC"), nitroveratryloxycarbonyl ("NVOC") and the like. Representative hydroxyl protecting groups include, but are not limited to, those where the hydroxyl group is either acylated (esterified) or alkylated such as benzyl and trityl ethers, as well as alkyl ethers, tetrahydropyranyl ethers, trialkylsilyl ethers (e.g., TMS or TIPS groups), glycol ethers, such as ethylene glycol and propylene glycol derivatives and allyl ethers.

The term "prodrug" is intended to encompass compounds which, under physiologic conditions, are converted into the therapeutically active agents of the present invention (e.g., a compound of formula I). A common method for making a prodrug is to include one or more selected moieties which are hydrolyzed under physiologic conditions to reveal the desired molecule. In other embodiments, the prodrug is converted by an enzymatic activity of the subject. For example, esters or carbonates (e.g., esters or carbonates of alcohols or carboxylic acids) are preferred prodrugs of the present invention. In certain embodiments, some or all of the compounds of formula I in a formulation represented above can be replaced with the corresponding suitable prodrug, e.g., wherein a hydroxyl in the parent compound is presented as an ester or a carbonate or carboxylic acid present in the parent compound is presented as an ester.

Compounds of the invention can have one or more asymmetric carbon atoms and can exist in the form of optically pure enantiomers, mixtures of enantiomers such as, for example, racemates, optically pure diastereoisomers, mixtures of diastereoisomers, diastereoisomeric race mates or mixtures of diastereoisomeric racemates. The optically active forms can be obtained for example by resolution of the racemates, by asymmetric synthesis or asymmetric chromatography (chromatography with a chiral adsorbents or eluant). That is, certain of the disclosed compounds may exist in various stereoisomeric forms.

Stereoisomers are compounds that differ only in their spatial arrangement. Enantiomers are pairs of stereoisomers whose mirror images are not superimposable, most commonly because they contain an asymmetrically substituted carbon atom that acts as a chiral center. "Enantiomer" means one of a pair of molecules that are mirror images of each other and are not superimposable. "Diastereomers" are stereoisomers that are not related as mirror images, most commonly because they contain two or more asymmetrically substituted carbon atoms and represent the configuration of substituents around one or more chiral carbon atoms. Enantiomers of a compound can be prepared, for example, by separating an enantiomer from a racemate using one or more well-known techniques and methods, such as, for example, chiral chromatography and separation methods based thereon. The appropriate technique and/or method for separating an enantiomer of a compound described herein from a racemic mixture can be readily determined by those of skill in the art.

"Geometric isomer" means isomers that differ in the orientation of substituent atoms in relationship to a carbon-carbon double bond, to a cycloalkyl ring, or to a bridged bicyclic system. Atoms (other than H) on each side of a carbon-carbon double bond may be in an E (substituents are on opposite sides of the carbon-carbon double bond) or Z (substituents are oriented on the same side) configuration. "R," "S," "S*," "R*," "E," "Z," "cis," and "trans," indicate configurations relative to the core molecule. Certain of the disclosed compounds may exist in atropisomeric forms. Atropisomers are stereoisomers resulting from hindered rotation about single bonds where the steric strain barrier to rotation is high enough to allow for the isolation of the conformers. The compounds of the invention may be prepared as individual isomers by either isomer-specific synthesis or resolved from an isomeric mixture. Conventional resolution techniques include forming the salt of a free base of each isomer of an isomeric pair using an optically active acid (followed by fractional crystallization and regeneration of the free base), forming the salt of the acid form of each isomer of an isomeric pair using an optically active amine (followed by fractional crystallization and regeneration of the free acid), forming an ester or amide of each of the isomers of an isomeric pair using an optically pure acid, amine or alcohol (followed by chromatographic separation and removal of the chiral auxiliary), or resolving an isomeric mixture of either a starting material or a final product using various well known chromatographic methods.

Diastereomeric purity by weight is the ratio of the weight of one diastereomer or over the weight of all the diastereomers. When the stereochemistry of a disclosed compound is named or depicted by structure, the named or depicted stereoisomer is at least about 60%, about 70%, about 80%, about 90%, about 99% or about 99.9% by weight relative to the other stereoisomers. When a single enantiomer is named or depicted by structure, the depicted or named enantiomer is at least about 60%, about 70%, about 80%, about 90%, about 99% or about 99.9% by weight optically pure. When a single diastereomer is named or depicted by structure, the depicted or named diastereomer is at least about 60%, about 70%, about 80%, about 90%, about 99% or about 99.9% by weight pure. Percent optical purity is the ratio of the weight of the enantiomer or over the weight of the enantiomer plus the weight of its optical isomer.

Percent purity by mole fraction is the ratio of the moles of the enantiomer (or diastereomer) or over the moles of the enantiomer (or diastereomer) plus the moles of its optical isomer. When the stereochemistry of a disclosed compound is named or depicted by structure, the named or depicted stereoisomer is at least about 60%, about 70%, about 80%, about 90%, about 99% or about 99.9% by mole fraction pure relative to the other stereoisomers. When a single enantiomer is named or depicted by structure, the depicted or named enantiomer is at least about 60%, about 70%, about 80%, about 90%, about 99% or about 99.9% by mole fraction pure. When a single diastereomer is named or depicted by structure, the depicted or named diastereomer is at least about 60%, about 70%, about 80%, about 90%, about 99% or about 99.9% by mole fraction pure.

When a disclosed compound is named or depicted by structure without indicating the stereochemistry, and the compound has at least one chiral center, it is to be understood that the name or structure encompasses either enantiomer of the compound free from the corresponding optical isomer, a racemic mixture of the compound or mixtures enriched in one enantiomer relative to its corresponding optical isomer. When a disclosed compound is named or depicted by structure without indicating the stereochemistry and has two or more chiral centers, it is to be understood that the name or structure encompasses a diastereomer free of other diastereomers, a number of diastereomers free from other diastereomeric pairs, mixtures of diastereomers, mixtures of diastereomeric pairs, mixtures of diastereomers in which one diastereomer is enriched relative to the other diastereomer(s) or mixtures of diastereomers in which one or more diastereomer is enriched relative to the other diastereomers. The invention embraces all of these forms.

As used herein, the term "pharmaceutically acceptable salt" means any pharmaceutically acceptable salt of the compound of formula (I). For example, pharmaceutically acceptable salts of any of the compounds described herein include those that are within the scope of sound medical judgment, suitable for use in contact with the tissues of humans and animals without undue toxicity, irritation, allergic response and are commensurate with a reasonable benefit/risk ratio. Pharmaceutically acceptable salts are well known in the art. For example, pharmaceutically acceptable salts are described in: Berge et al., *J. Pharmaceutical Sciences* 66:1-19, 1977 and in Pharmaceutical Salts: Properties, Selection, and Use, (Eds. P. H. Stahl and C. G. Wermuth), Wiley-VCH, 2008. The salts can be prepared in situ during the final isolation and purification of the compounds described herein or separately by reacting a free base group with a suitable organic acid.

The compounds of the invention may have ionizable groups so as to be capable of preparation as pharmaceutically acceptable salts. These salts may be acid addition salts involving inorganic or organic acids or the salts may, in the case of acidic forms of the compounds of the invention be prepared from inorganic or organic bases. Frequently, the compounds are prepared or used as pharmaceutically acceptable salts prepared as addition products of pharmaceutically acceptable acids or bases. Suitable pharmaceutically acceptable acids and bases and methods for preparation of the appropriate salts are well-known in the art. Salts may be prepared from pharmaceutically acceptable non-toxic acids and bases including inorganic and organic acids and bases.

Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, and valerate salts. Representative alkali or alkaline earth metal salts include sodium, lithium, potassium, calcium, and magnesium, as well as nontoxic ammonium, quaternary ammonium, and amine cations, including, but not limited to ammonium, tetramethylammonium, tetraethylammonium, methylamine, dimethylamine, trimethylamine, triethylamine, and ethylamine.

The term "subject" to which administration is contemplated includes, but is not limited to, humans (i.e., a male or female of any age group, e.g., a pediatric subject (e.g., infant, child, adolescent) or adult subject (e.g., young adult, middle-aged adult or senior adult)) and/or other primates (e.g., cynomolgus monkeys, rhesus monkeys); mammals, including commercially relevant mammals such as cattle, pigs, horses, sheep, goats, cats, and/or dogs; and/or birds, including commercially relevant birds such as chickens, ducks, geese, quail, and/or turkeys. Preferred subjects are humans.

As used herein, a therapeutic that "prevents" a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample.

The term "treating" includes prophylactic and/or therapeutic treatments. The term "prophylactic or therapeutic" treatment is art-recognized and includes administration to the subject of one or more of the disclosed compositions. If it is administered prior to clinical manifestation of the unwanted condition (e.g., disease or other unwanted state of the subject) then the treatment is prophylactic (i.e., it protects the subject against developing the unwanted condition), whereas if it is administered after manifestation of the unwanted condition, the treatment is therapeutic, (i.e., it is intended to diminish, ameliorate, or stabilize the existing unwanted condition or side effects thereof).

In treatment, the object is to prevent or slow down (lessen) an undesired physiological condition, disorder, or disease, or obtain beneficial or desired clinical results. Beneficial or desired clinical results include, but are not limited to, alleviation of symptoms; diminishment of the extent of a condition, disorder, or disease; stabilized (i.e., not worsening) state of condition, disorder, or disease; delay in onset or slowing of condition, disorder, or disease progression; amelioration of the condition, disorder, or disease state or remission (whether partial or total), whether detectable or undetectable; an amelioration of at least one measurable physical parameter, not necessarily discernible by the patient; or enhancement or improvement of condition, disorder, or disease. Treatment includes eliciting a clinically significant response without excessive levels of side effects. Treatment also includes prolonging survival as compared to expected survival if not receiving treatment.

Compounds

Disclosed herein are compounds of Formula I, or a pharmaceutically acceptable salt thereof:

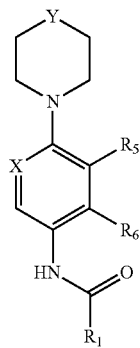

I wherein:
X is N or CH;
Y is $NR_2$ or $CR_3R_4$;
$R_1$ is selected from alkyl, cycloalkyl, aryl and heteroaryl;
$R_2$ is selected from acyl, aryl, and heteroaryl;
$R_3$ is selected from H, alkyl, and heterocyclyl;
$R_4$ is selected from H, alkyl and amido; and
one of $R_5$ and $R_6$ is —COOH and the other is H.

Methods of Use

In certain embodiments, provided herein are methods of treating inflammatory bowel disease, comprising administering to a subject a compound of Formula I or a pharmaceutically acceptable salt thereof:

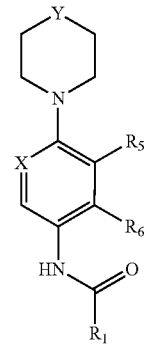

I wherein:
X is N or CH;
Y is $NR_2$ or $CR_3R_4$;
$R_1$ is selected from alkyl, cycloalkyl, aryl and heteroaryl;
$R_2$ is selected from acyl, aryl, and heteroaryl;
$R_3$ is selected from H, alkyl, and heterocyclyl;
$R_4$ is selected from H, alkyl and amido; and
one of $R_5$ and $R_6$ is —COOH and the other is H.

In certain embodiments, the inflammatory bowel disease is selected from Crohn's disease, ulcerative colitis, microscopic colitis, collagenous colitis, lymphocytic colitis, diversion colitis, Behcet's disease and indeterminate colitis. In certain embodiments, the inflammatory bowel disease is Crohn's disease or ulcerative colitis. In certain embodiments, the inflammatory bowel disease is Crohn's disease. In other embodiments, the inflammatory bowel disease is Crohn's disease.

In certain embodiments, provided herein are methods of modulating CARD9, comprising administering to a subject a compound of Formula I or a pharmaceutically acceptable salt thereof:

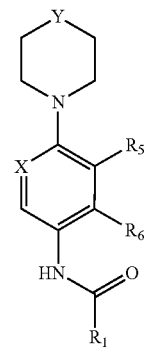

I wherein:
X is N or CH;
Y is $NR_2$ or $CR_3R_4$;
$R_1$ is selected from alkyl, cycloalkyl, aryl and heteroaryl;
$R_2$ is selected from acyl, aryl, and heteroaryl;
$R_3$ is selected from H, alkyl, and heterocyclyl;
$R_4$ is selected from H, alkyl and amido; and
one of $R_5$ and $R_6$ is —COOH and the other is H.

In certain embodiments, modulating CARD9 comprises increasing the activity of a protective variant of CARD9. In some embodiments, the protective variant of CARD9 is CARD9Δ11. In certain embodiments, modulating CARD9 comprises decreasing the activity of a risk variant of CARD9. In other embodiments, modulating CARD9 comprises inhibiting TRIM62-mediated ubiquitinylation of CARD9.

In certain embodiments, X is N. In other embodiments, X is CH. In some embodiments, Y is $NR_2$. In other embodiments, Y is $CR_3R_4$.

In certain embodiments, $R_1$ is selected from methyl, butyl, cyclopropyl, phenyl, and thiophenyl. In certain embodiments, $R_1$ is phenyl substituted with one or more substituents selected from methyl, fluoro, and chloro. In some embodiments, Y is $NR_2$ and $R_2$ is selected from —C(O)Me, phenyl and pyridyl. In other embodiments, Y is $CR_3R_4$ and $R_3$ is selected from H, methyl, ethyl, and piperidinyl. Here, the methyl and ethyl are optionally substituted with piperidinyl or pyrrolidinyl.

In some embodiments, $R_4$ is H or —C(O)$NH_2$. In certain embodiments, Y is $CR_3R_4$, $R_3$ is piperidinyl and $R_4$ is —C(O)$NH_2$. In some embodiments, $R_5$ is —COOH and $R_6$ is H. In other embodiments, $R_5$ is H and $R_6$ is —COOH.

In certain embodiments, the compound of Formula I is selected from:

(1)

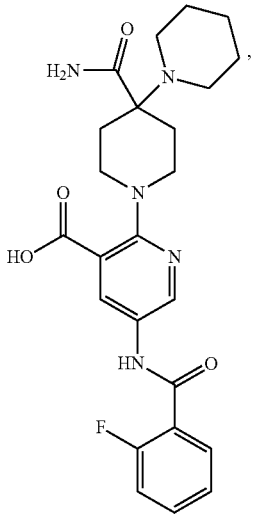

(2)

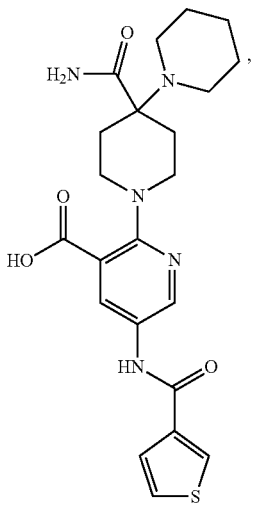

-continued (3)

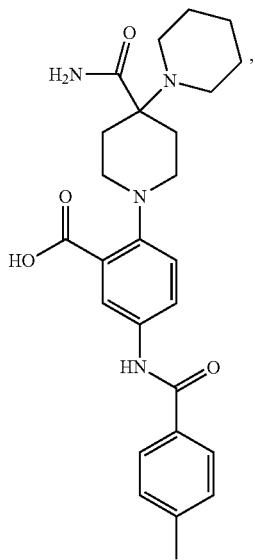

(4)

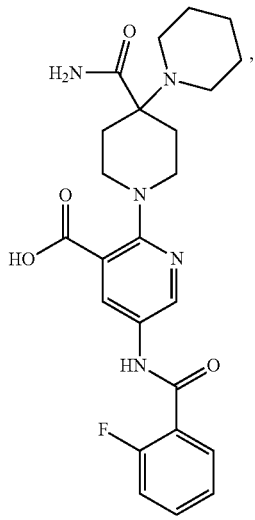

(5)

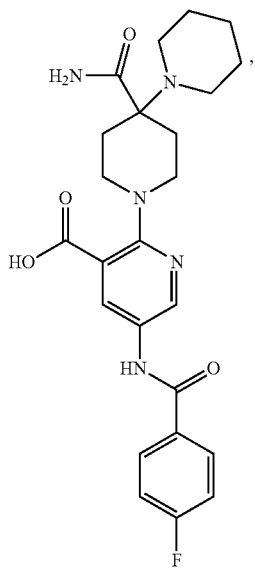

(6)
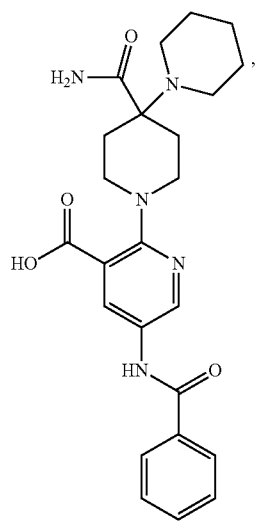
(7)
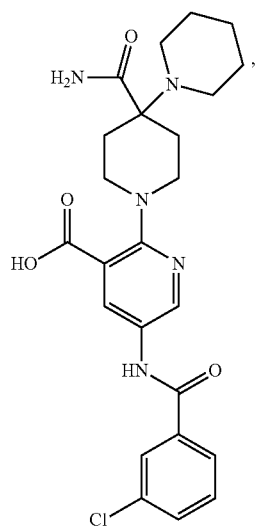
(8)
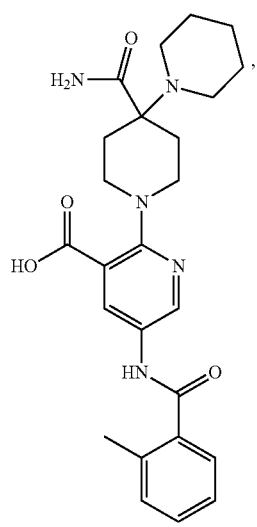
(9)
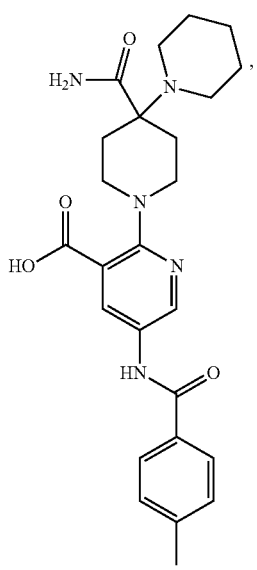
(10)
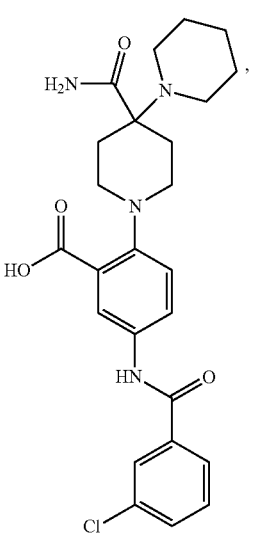
(11)
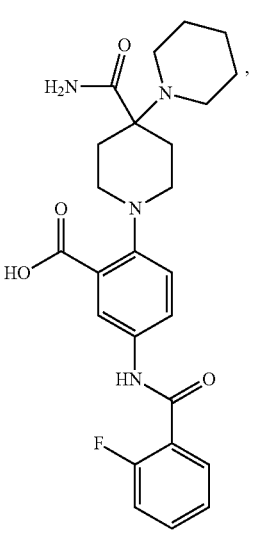

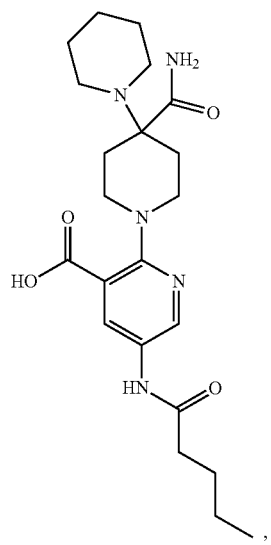
(12)
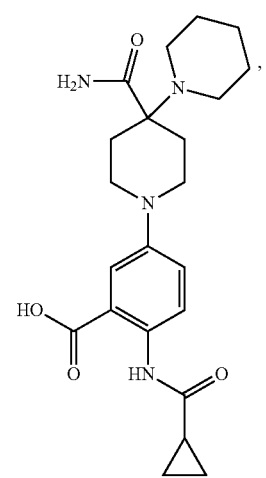
(13)
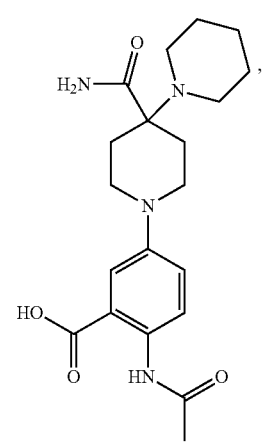
(14)
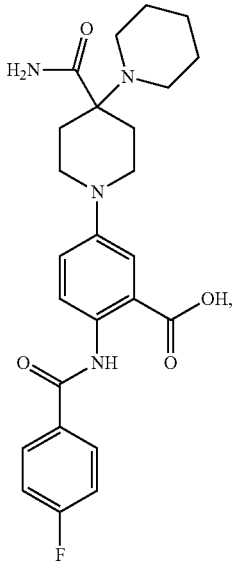
(15)
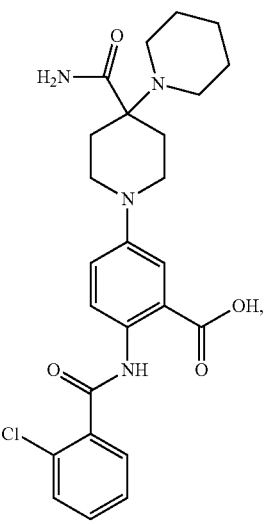
(16)
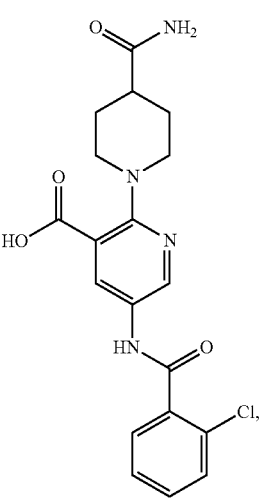
(17)

(18)
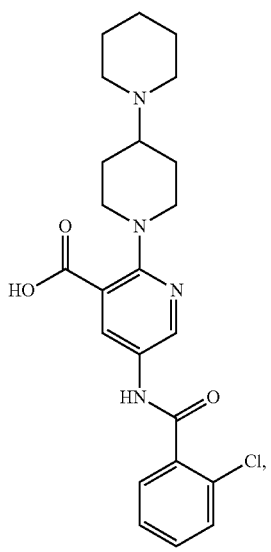
(19)
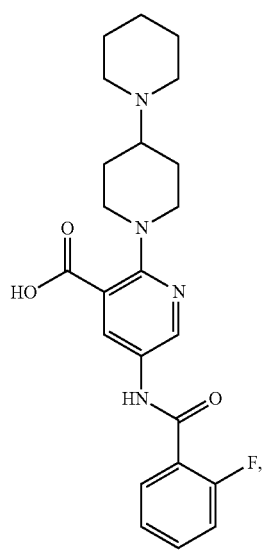
(20)
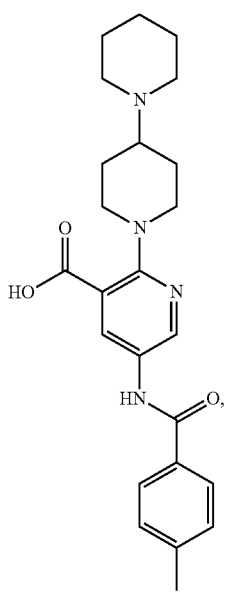
(21)
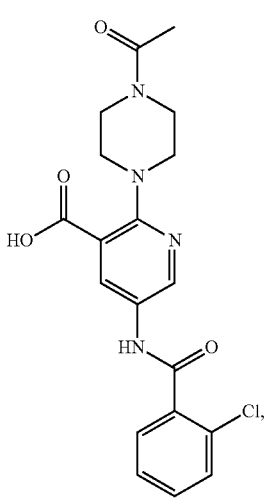

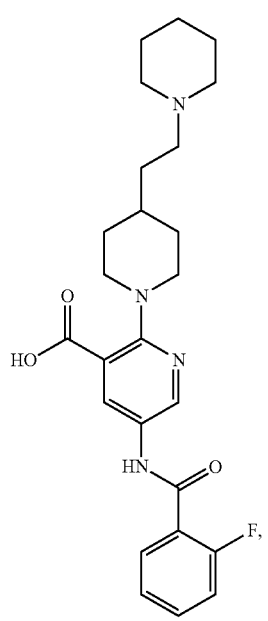
(22)
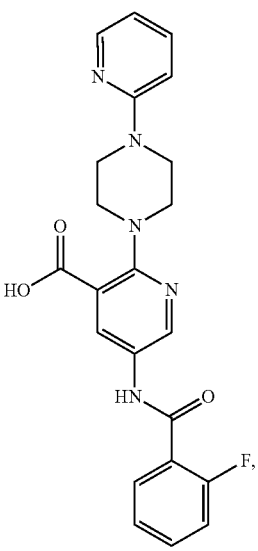
(24)
(25)
(23)
(26)
and

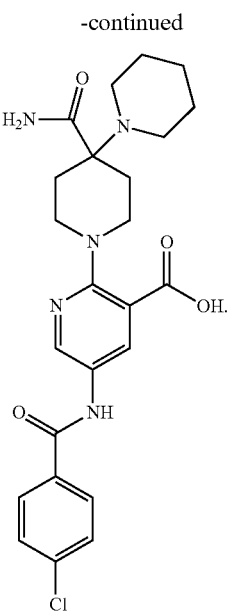

(27)

CARD9 plays a key role in mediating innate immune signaling from C-type-Lectin receptors (CLRs), such as Dectin-1 and Mincle, which are responsible for recognition of fungi and mycobacteria in intestinal myeloid cells and dendritic cells. (Gross, O. et al. Card9 controls a non-TLR signalling pathway for innate anti-fungal immunity. 2006 *Nature* 442, 651-656.) The CARD9 gene has both risk and protective alleles that can influence the course of intestinal disease, such as inflammatory bowel syndrome. In wild-type CARD9, E3 ubiquitin ligase TRIM62 specifically interacts with WT CARD9 C-terminal domain (CTD) and activates CARD9 via K27 ubiquitinylation. The risk variant of CARD9 is associated with increased NF-κB-mediated cytokine production in dendritic cells upon exposure to microbial ligands. In contrast, the protective variant, CARD9Δ11, lacks a functional CTD and is thus unable to recruit the E3 ubiquitin ligase TRIM62 for subsequent activation of NF-κB. (Beaudoin, M. et al. Deep resequencing of GWAS loci identifies rare variants in CARD9, IL23R and RNF186 that are associated with ulcerative colitis. 2013 *PLoS genetics* 9, e1003723; Cao, Z. et al. Ubiquitin Ligase TRIM62 Regulates CARD9-Mediated Anti-fungal Immunity and Intestinal Inflammation. *Immunity* 2015 43, 715-726.)

The disclosed compounds demonstrate biological activity in directly and selectively binding CARD9, disrupting TRIM62 recruitment, and inhibiting TRIM62-mediated ubiquitinylation of CARD9. These CARD9-modulating compounds also selectively inhibit NF-κB activation in CARD9-dependent pathways. Their activity is similar to the effect of protective variant CARD9Δ11. Provided herein are modulators of CARD9 that are selective disruptors of the CARD9-TRIM62 protein-protein interaction (PPI) in vitro. These compounds also act in vivo to modulate CARD9 activity in a monocytic cell line THP-1 and primary immune cells (BMDCs).

Pharmaceutical Compositions

The compositions and methods of the present invention may be utilized to treat a subject in need thereof. In certain embodiments, the subject is a mammal such as a human, or a non-human mammal. When administered to subject, such as a human, the composition or the compound is preferably administered as a pharmaceutical composition comprising, for example, a compound of the invention and a pharmaceutically acceptable carrier. Pharmaceutically acceptable carriers are well known in the art and include, for example, aqueous solutions such as water or physiologically buffered saline or other solvents or vehicles such as glycols, glycerol, oils such as olive oil, or injectable organic esters. In a preferred embodiment, when such pharmaceutical compositions are for human administration, particularly for invasive routes of administration (i.e., routes, such as injection or implantation, that circumvent transport or diffusion through an epithelial barrier), the aqueous solution is pyrogen-free, or substantially pyrogen-free. The excipients can be chosen, for example, to effect delayed release of an agent or to selectively target one or more cells, tissues or organs. The pharmaceutical composition can be in dosage unit form such as tablet, capsule (including sprinkle capsule and gelatin capsule), granule, lyophile for reconstitution, powder, solution, syrup, suppository, injection or the like. The composition can also be present in a transdermal delivery system, e.g., a skin patch. The composition can also be present in a solution suitable for topical administration, such as an eye drop.

A pharmaceutically acceptable carrier can contain physiologically acceptable agents that act, for example, to stabilize, increase solubility or to increase the absorption of a compound such as a compound of the invention. Such physiologically acceptable agents include, for example, carbohydrates, such as glucose, sucrose or dextrans, antioxidants, such as ascorbic acid or glutathione, chelating agents, low molecular weight proteins or other stabilizers or excipients. The choice of a pharmaceutically acceptable carrier, including a physiologically acceptable agent, depends, for example, on the route of administration of the composition. The preparation or pharmaceutical composition can be a self emulsifying drug delivery system or a self microemulsifying drug delivery system. The pharmaceutical composition (preparation) also can be a liposome or other polymer matrix, which can have incorporated therein, for example, a compound of the invention. Liposomes, for example, which comprise phospholipids or other lipids, are nontoxic, physiologically acceptable and metabolizable carriers that are relatively simple to make and administer.

The phrase "pharmaceutically acceptable" is employed herein to refer to those compounds, materials, compositions, and/or dosage forms which are, within the scope of sound medical judgment, suitable for use in contact with the tissues of a subject without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the subject. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11)

polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

A pharmaceutical composition (preparation) can be administered to a subject by any of a number of routes of administration including, for example, orally (for example, drenches as in aqueous or non-aqueous solutions or suspensions, tablets, capsules (including sprinkle capsules and gelatin capsules), boluses, powders, granules, pastes for application to the tongue); absorption through the oral mucosa (e.g., sublingually); anally, rectally or vaginally (for example, as a pessary, cream or foam); parenterally (including intramuscularly, intravenously, subcutaneously or intrathecally as, for example, a sterile solution or suspension); nasally; intraperitoneally; subcutaneously; transdermally (for example as a patch applied to the skin); and topically (for example, as a cream, ointment or spray applied to the skin, or as an eye drop). The compound may also be formulated for inhalation. In certain embodiments, a compound may be simply dissolved or suspended in sterile water. Details of appropriate routes of administration and compositions suitable for same can be found in, for example, U.S. Pat. Nos. 6,110,973, 5,763,493, 5,731,000, 5,541,231, 5,427,798, 5,358,970 and 4,172,896, as well as in patents cited therein.

The formulations may conveniently be presented in unit dosage form and may be prepared by any methods well known in the art of pharmacy. The amount of active ingredient which can be combined with a carrier material to produce a single dosage form will vary depending upon the subject being treated, the particular mode of administration. The amount of active ingredient that can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an active compound, such as a compound of the invention, with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules (including sprinkle capsules and gelatin capsules), cachets, pills, tablets, lozenges (using a flavored basis, usually sucrose and acacia or tragacanth), lyophile, powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. Compositions or compounds may also be administered as a bolus, electuary or paste.

To prepare solid dosage forms for oral administration (capsules (including sprinkle capsules and gelatin capsules), tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; (10) complexing agents, such as, modified and unmodified cyclodextrins; and (11) coloring agents. In the case of capsules (including sprinkle capsules and gelatin capsules), tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions, such as dragees, capsules (including sprinkle capsules and gelatin capsules), pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms useful for oral administration include pharmaceutically acceptable emulsions, lyophiles for reconstitution, microemulsions, solutions, suspensions, syrups and elixirs. In addition to the active ingredient, the liquid dosage forms may contain inert diluents commonly used in the art, such as, for example, water or other solvents, cyclodextrins and derivatives thereof, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions for rectal, vaginal, or urethral administration may be presented as a suppository, which may be prepared by mixing one or more active compounds with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the pharmaceutical compositions for administration to the mouth may be presented as a mouthwash, or an oral spray, or an oral ointment.

Alternatively or additionally, compositions can be formulated for delivery via a catheter, stent, wire, or other intraluminal device. Delivery via such devices may be especially useful for delivery to the bladder, urethra, ureter, rectum, or intestine.

Formulations which are suitable for vaginal administration also include pessaries, tampons, creams, gels, pastes, foams or spray formulations containing such carriers as are known in the art to be appropriate.

Dosage forms for the topical or transdermal administration include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The ointments, pastes, creams and gels may contain, in addition to an active compound, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an active compound, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the active compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention. Exemplary ophthalmic formulations are described in U.S. Publication Nos. 2005/0080056, 2005/0059744, 2005/0031697 and 2005/004074 and U.S. Pat. No. 6,583,124, the contents of which are incorporated herein by reference. If desired, liquid ophthalmic formulations have properties similar to that of lacrimal fluids, aqueous humor or vitreous humor or are compatable with such fluids. A preferred route of administration is local administration (e.g., topical administration, such as eye drops, or administration via an implant).

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

Pharmaceutical compositions suitable for parenteral administration comprise one or more active compounds in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle.

Injectable depot forms are made by forming microencapsulated matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue.

For use in the methods of this invention, active compounds can be given per se or as a pharmaceutical composition containing, for example, 0.1 to 99.5% (more preferably, 0.5 to 90%) of active ingredient in combination with a pharmaceutically acceptable carrier.

Methods of introduction may also be provided by rechargeable or biodegradable devices. Various slow release polymeric devices have been developed and tested in vivo in recent years for the controlled delivery of drugs, including proteinacious biopharmaceuticals. A variety of biocompatible polymers (including hydrogels), including both biodegradable and non-degradable polymers, can be used to form an implant for the sustained release of a compound at a particular target site.

Actual dosage levels of the active ingredients in the pharmaceutical compositions may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound or combination of compounds employed, or the ester, salt or amide thereof, the route of administration, the time of administration, the rate of excretion of the particular compound(s) being employed, the duration of the treatment, other drugs, compounds and/or materials used in combination with the particular compound(s) employed, the age, sex, weight, condition, general health and prior medical history of the subject being treated, and like factors well known in the medical arts.

A physician or veterinarian having ordinary skill in the art can readily determine and prescribe the therapeutically effective amount of the pharmaceutical composition required. For example, the physician or veterinarian could start doses of the pharmaceutical composition or compound at levels lower than that required in order to achieve the desired therapeutic effect and gradually increase the dosage until the desired effect is achieved. By "therapeutically effective amount" is meant the concentration of a compound that is sufficient to elicit the desired therapeutic effect. It is generally understood that the effective amount of the compound will vary according to the weight, sex, age, and medical history of the subject. Other factors which influence the effective amount may include, but are not limited to, the severity of the subject's condition, the disorder being treated, the stability of the compound, and, if desired, another type of therapeutic agent being administered with the compound of the invention. A larger total dose can be delivered by multiple administrations of the agent. Methods to determine efficacy and dosage are known to those skilled in the art (Isselbacher et al. (1996) Harrison's Principles of Internal Medicine 13 ed., 1814-1882, herein incorporated by reference).

In general, a suitable daily dose of an active compound used in the compositions and methods of the invention will be that amount of the compound that is the lowest dose effective to produce a therapeutic effect. Such an effective dose will generally depend upon the factors described above.

If desired, the effective daily dose of the active compound may be administered as one, two, three, four, five, six or more sub-doses administered separately at appropriate intervals throughout the day, optionally, in unit dosage forms. In certain embodiments of the present invention, the active compound may be administered two or three times daily. In preferred embodiments, the active compound will be administered once daily.

In certain embodiments, the dosing follows a 3+3 design. The traditional 3+3 design requires no modeling of the dose-toxicity curve beyond the classical assumption for cytotoxic drugs that toxicity increases with dose. This rule-based design proceeds with cohorts of three patients; the first cohort is treated at a starting dose that is considered to be safe based on extrapolation from animal toxicological data, and the subsequent cohorts are treated at increasing dose levels that have been fixed in advance. In some embodiments, the three doses of a compound of formula (I) range from about 100 mg to about 1000 mg orally, such as about 200 mg to about 800 mg, such as about 400 mg to about 700 mg, such as about 100 mg to about 400 mg, such as about 500 mg to about 1000 mg, and further such as about 500 mg to about 600 mg. Dosing can be three times a day when taken with without food, or twice a day when taken with food. In certain embodiments, the three doses of a compound of formula (I) range from about 400 mg to about 800 mg, such as about 400 mg to about 700 mg, such as about 500 mg to about 800 mg, and further such as about 500 mg to about 600 mg twice a day. In certain preferred embodiments, a dose of greater than about 600 mg is dosed twice a day.

If none of the three patients in a cohort experiences a dose-limiting toxicity, another three patients will be treated at the next higher dose level. However, if one of the first three patients experiences a dose-limiting toxicity, three more patients will be treated at the same dose level. The dose escalation continues until at least two patients among a cohort of three to six patients experience dose-limiting toxicities (ie, ≥about 33% of patients with a dose-limiting toxicity at that dose level). The recommended dose for phase II trials is conventionally defined as the dose level just below this toxic dose level.

In certain embodiments, the dosing schedule can be about 40 $mg/m^2$ to about 100 $mg/m^2$, such as about 50 $mg/m^2$ to about 80 $mg/m^2$, and further such as about 70 $mg/m^2$ to about 90 $mg/m^2$ by IV for 3 weeks of a 4 week cycle.

In certain embodiments, compounds of the invention may be used alone or conjointly administered with another type of therapeutic agent. As used herein, the phrase "conjoint administration" refers to any form of administration of two or more different therapeutic compounds such that the second compound is administered while the previously administered therapeutic compound is still effective in the body (e.g., the two compounds are simultaneously effective in the subject, which may include synergistic effects of the two compounds). For example, the different therapeutic compounds can be administered either in the same formulation or in a separate formulation, either concomitantly or sequentially. In certain embodiments, the different therapeutic compounds can be administered within one hour, 12 hours, 24 hours, 36 hours, 48 hours, 72 hours, or a week of one another. Thus, a subject who receives such treatment can benefit from a combined effect of different therapeutic compounds.

In certain embodiments, conjoint administration of compounds of the invention with one or more additional therapeutic agent(s) (e.g., one or more additional chemotherapeutic agent(s)) provides improved efficacy relative to each individual administration of the compound of the invention (e.g., compound of formula I or Ia) or the one or more additional therapeutic agent(s). In certain such embodiments, the conjoint administration provides an additive effect, wherein an additive effect refers to the sum of each of the effects of individual administration of the compound of the invention and the one or more additional therapeutic agent(s).

This invention includes the use of pharmaceutically acceptable salts of compounds of the invention in the compositions and methods of the present invention. In certain embodiments, contemplated salts of the invention include, but are not limited to, alkyl, dialkyl, trialkyl or tetra-alkyl ammonium salts. In certain embodiments, contemplated salts of the invention include, but are not limited to, L-arginine, benenthamine, benzathine, betaine, calcium hydroxide, choline, deanol, diethanolamine, diethylamine, 2-(diethylamino)ethanol, ethanolamine, ethylenediamine, N-methylglucamine, hydrabamine, 1H-imidazole, lithium, L-lysine, magnesium, 4-(2-hydroxyethyl)morpholine, piperazine, potassium, 1-(2-hydroxyethyl)pyrrolidine, sodium, triethanolamine, tromethamine, and zinc salts. In certain embodiments, contemplated salts of the invention include, but are not limited to, Na, Ca, K, Mg, Zn or other metal salts.

The pharmaceutically acceptable acid addition salts can also exist as various solvates, such as with water, methanol, ethanol, dimethylformamide, and the like. Mixtures of such solvates can also be prepared. The source of such solvate can be from the solvent of crystallization, inherent in the solvent of preparation or crystallization, or adventitious to such solvent.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water-soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like.

EXAMPLES

Synthetic Procedures

One of skill in the art will readily recognize that compounds of the present invention can be synthesized using routine chemical synthetic methods. The compounds disclosed herein were derived from diversity-oriented synthesis (Burke, M. D. & Schreiber, S. L. A planning strategy for diversity-oriented synthesis. 2004 *Angewandte Chemie* 43, 46-58) or purchased from vendors (ChemBridge autophagy-focused set; Maybridge; ChemDiv autophagy-focused library; WuXi; MLP set).

Materials and Methods

Flag-StrepII-CARD9 and TRIM62 were purified as described (Cao et al). TRIM62ΔRING and B30.2/SPRY were expressed in Sf9 cells in pFastBac as His$_8$ fusion. For Luminex assay, HEK293F cells were transfected with 3XMyc-TRIM62 in pCMV and separately with Flag-CARD9 in pcDNA4/TO. Anti-Myc tag antibody (9E10) was conjugated to the beads and used for TRIM62 affinity capture from cleared lysates. Following the incubation with compounds, Flag-CARD9 lysate was added; after a series of washes and secondary PE-conjugated antibody incubation, readout was performed on MagPlex instruments.

Biological Assays

Protein Constructs and Purification

Full-length Flag-StrepII-CARD9 for AlphaLISA, DSF and NMR assays was expressed as previously described (Cao et al.). Full-length TRIM62 for AlphaLISA assay was expressed as previously described (Cao et al.). TRIM62ΔRING was expressed in Sf9 cells in pFastBac construct as His8 fusion, and purified on Ni affinity column followed by size exclusion chromatography. B30.2/SPRY domain of TRIM62 was expressed as His8-MBP fusion in Sf9 cells and purified on Ni affinity column followed by size exclusion chromatography. Full-length CTD416-536 and truncated constructs CTD416-516, CTD416-496 and CTD416-476 were expressed as previously described (Cao et al.). The CARD domain was expressed as His8 fusion in *E. coli* (BL21(DE3)) and purified on Ni affinity column followed by size exclusion chromatography.

Luminex Bead-Based ELISA Assay

HEK293F (Life Technologies, R790-07) cells were grown in Freestyle media (Cat. #12338) according to manufacturer's instructions. Cells were transiently transfected with 3XMyc-TRIM62 in pCMV and separately with Flag-CARD9 in pcDNA4/TO. Anti-Myc tag antibody (9E10, Sigma) was conjugated to the Luminex beads (10 spectral range beads in 10 separate reactions) using Pierce reagents/Luminex coupling kit. Flag-CARD9 and Myc-TRIM62 transfected cells were separately lysed in the lysis buffer (50 mM Tris pH 7.4, 150 mM NaCl, 0.5% NP40, protease inhibitors (Complete, Roche, 11873580001), phosphatase inhibitors (PhosStop, Roche, 4906845001)) and cleared by centrifugation at 10,000 g. Cleared TRIM62 lysates were added to the beads for Myc-mediated capture, incubated at room temperature for 1 hr, then washed 1x and reconstituted in 1% BSA in PBS.

Screening compounds were pre-dispensed into assay-ready plates (twintecc, Eppendorf; 50 nl of 10 mM compound stock in DMSO per well). Cleared CARD9 lysate (20 μl per well) was added to the assay-ready plate and pre-incubated with the screening compounds for 30 min before addition of TRIM62-bound beads (300 beads per well, in 5 μl of 1% BSA in PBS). Plates were mixed on Bioshake IQ at 2400 rpm for 2 min and incubated for 40 min at room temperature. Plates were then washed on Biomek NX$^P$ instrument with magnetic plate holders 1× with 1% BSA in PBS. Each 10 plates with non-identical spectral regions of beads were combined into one deep-well plate, and incubated with Flag-PE antibody conjugate (Abcam, ab72469) at the final dilution 1:400 for 1 hr. After 1× wash with 1% BSA in PBS, the readout was performed on Luminex MagPlex instruments with standard operating protocol. Bead quantity per well was employed as quality control measure, wells with bead count less than 20 were rejected from the analysis.

Differential Scanning Fluorimetry (DSF)

DSF assay was performed on a Roche LightCycler 480 II with ramp speed of 4.8° C. per min and 12 acquisitions per ° C. Experimental buffer was 50 mM Tris, pH 7.5, 150 mM NaCl, 0.5 mM TCEP. Freshly purified or flash-frozen in 10% glycerol protein was dialyzed overnight into experimental buffer. Purified Flag-StrepII-CARD9 (2.5 μM) or TRIM62ΔRING (2.5 μM) were mixed with the corresponding small molecule (100 μM) and SYPRO dye (Life Technologies, 1:1000 dilution) in 384-well polypropylene PCR plates (10 μl per well). As part of the assay optimization, lower concentrations of protein (0.8-2.5 μM) and higher concentrations of the compounds (100-400 μM) were all successfully tested.

The plates were sealed and heated in the instrument across a temperature range of 25° C.-95° C. The minimum of the negative first derivative curve was used to estimate the protein melting temperature (Tm).

Saturation Transfer Difference Nuclear Magnetic Resonance (STD NMR)

STD experiments were performed using CARD9 and TRIM62ΔRING purified by size exclusion on a S200 column in a completely deuterated buffer since CARD9 precipitation occurs during dialysis or concentration. Proteins were diluted to 5 μM and compounds were at 200 μM with 2% $d_6$-DMSO. Experiments were performed on a Bruker spectrometer equipped with a cryoprobe and operating at a proton frequency of 600 MHz. Data were collected at 280K in interleaved mode as described (Mayer, M. M., B. Characterization of Ligand Binding by Saturation Transfer Difference NMR Spectroscopy. *Angewandte Chemie* 1999 38, 1784-1788) with 16 scans, 14 ppm sweep width, 2.2 seconds saturation at a power level of 6.78 W and offset of −0.25 ppm.

AlphaLISA and Western Blot Ubiquitinylation Assay

FlagStrep-CARD9 and TRIM62 were expressed and purified as previously described (Cao et al.). Assay-ready plates containing 80 nl of 10 mM compound in DMSO were used. Ubiquitinylation reactions contained 12.5 nM Flag-Strep-CARD9, 1.25 nM TRIM62, 500 nM ubiquitin, 10 nM UBE1 (LifeSensors), 200 nM UBE2D2 (LifeSensors), 50 mM Tris pH=7.5, 5 mM MgCl2, 2.5 mM ATP, 1 mM DTT, 0.005% Tween-20 in a final volume of 10 μl. To assemble reactions, all reaction components except ubiquitin and Trim62 were combined and dispensed at a 2× concentration in a volume of 5 μl using a Multi-Drop Combi Reagent Dispenser. Reactions were initiated by added ubiquitin and TRIM62 at a 2× concentration in a volume of 5 μL in the same manner. The reactions were incubated at ambient temperature for 90 min then stopped by the addition of 10 μl of 2× quench/detect solution using a 16-ViaFlow dispenser. The 2× quench/detect solution contained 100 mM HEPES pH=7.5, 300 mM NaCl, 0.01% Tween 20, 30 mM ETDA, 40 μg/ml Streptavidin-Donor beads, 10 μg/ml α-Flag-Acceptor beads (both from PerkinElmer) and 100 nM biotin-TUBE1 (LifeSensors). Plates were incubated at RT for an additional 1 h then read on a PerkinElmer Envision.

For western blot detection, ubiquitinylation reactions contained 250 nM Flag-Strep-CARD9, 5 nM TRIM62, 5 μM of HA-tagged ubiquitin (Boston Biochem), 25 nM UBE1 (LifeSensors), 300 nM UBE2D2 (LifeSensors), 50 mM Tris pH=7.5, 5 mM MgCl$_2$, 2.5 mM ATP, 1 mM DTT in a final volume of 20 μl. Reactions were quenched by the addition of the LDS sample buffer with 50 mM DTT. HA antibody F-7 (Santa Cruz) was used for the detection of polyubiquitin chains, and Flag M2 antibody from Sigma was used to detect Flag-StrepII-CARD9 as a loading control.

Cell Culture and Primary Cells Isolation

THP-1 and HEK293T cells were from ATCC and cultured according to ATCC instructions. Cell cultures were regularly checked for mycoplasma contamination using a mycoplasma PCR test. BMDCs were isolated from femur and tibia of C57B/6 mice by harvesting bone marrows followed by hypotonic red blood cell lysis. Obtained bone marrow cells were cultured in DMEM (10% FBS, 1% penicillin/streptomycin, 1% glutamin) with 25 ng/ml GM-CSF.

Phospho-IKK FACS

For phospho-IKK FACS analysis, the BMDCs were plated on day 7 in U bottom 96-well plates at 150,000 cells/well in DMEM, 10% FBS, 1% penicillin/streptomycin, glutamine and GM-CSF the day before the assay. Growth media was replaced with reduced serum media (2% FBS), at this time compound 9 was added to the appropriate wells (at 200 μM) and cells were incubated for 2 hours. Cells were stimulated with 50 μg/ml scleroglucan (Invivogen) or 100 ng/ml LPS (Sigma) for the indicated times at 37° C. At the end of the incubation, media was aspirated and cells were fixed in 4% PFA for 10 min at 37° C.; then resuspended in blocking buffer (3% BSA in permeabilization buffer, eBioscience). Cells were harvested by scraping with pipette tips, spun at 350 g for 3 min, resuspended in staining cocktail (blocking buffer+rat anti-IA/IE APC 1:1000, rabbit anti phospho-IKK PE 1:50) and stained at room temperature in the dark for 60 min. Cells were washed 1x in blocking buffer and resuspended in FACS buffer (PBS, 2% FBS). FACS analysis was run on Cytoflex instrument (Beckman Coulter) and analyzed using FlowJo software by sequentially gating on live/single cells/MHCII high cell population.

CARD9 Rescue in THP-1 Cell Lines and NF-κB Reporter Assay

CARD9 KO THP-1 cells were generated by a CRIPSR-based approach as previously described (Cao et al.). For the NF-κB luciferase assay, CARD9 KO or WT THP-1 cells lines were transduced with Dectin-1 (NM 022570) and a lentivirus-based NF-κB luciferase reporter, containing NF-κB responsive element upstream of minimal promoter and Luc2P54. CARD9 KO cells overexpressing Dectin-1 and the NF-κB luciferase reporter were rescued with indicated CARD9 constructs. For compound treatment, Compound 9 was pre-incubated with Dectin-1, NF-κB reporter expressing THP-1 cells for 2 hours, followed by stimulation with scleroglucan (50 μg/ml), whole glucan particles (WGP dispersible, Invivogen, 50 μg/ml), or LPS (100 ng/ml). Reporter luciferase activity was measured using Steadylite Plus reagent (PerkinElmer).

Biological Examples

Example 1

Luminex Bead-Based ELISA Assay and AlphaLISA Ubiquitinylation Assay

FIG. 1 indicates that compounds 9 (FIG. 1A), 6 (FIG. 1B), 7 (FIG. 1C), and 27 (FIG. 1D) are dose-dependent inhibitors in a CARD9-TRIM62 protein-protein interaction assay.

Testing the compounds against CARD9-BCL10 PPI inhibition illustrated the selectivity of CARD9-TRIM62 PPI inhibition.

Figure 2A:
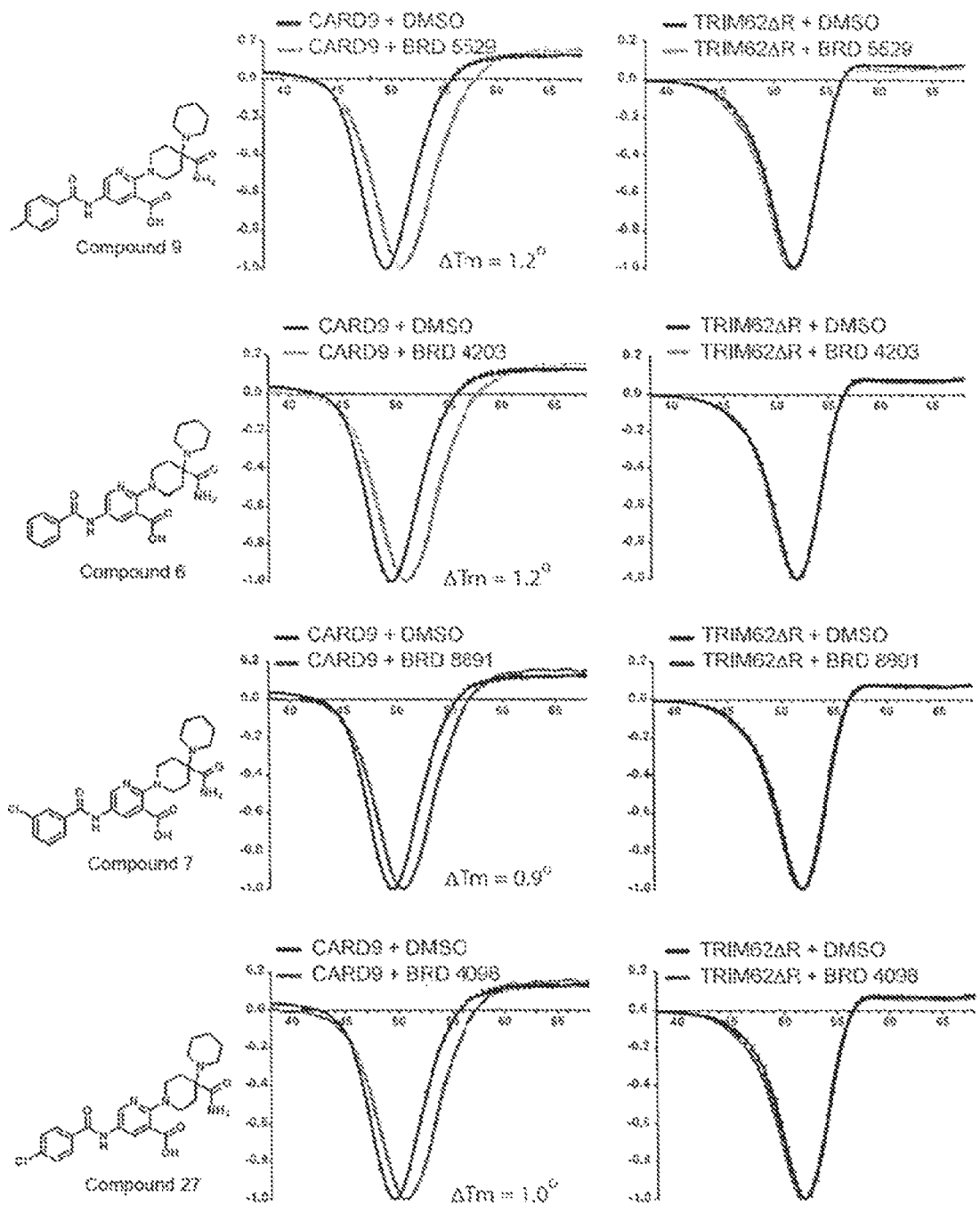
FIG. 2A illustrates that certain compounds of the invention directly bind CARD9, but not TRIM62, as evidenced by thermal shift using Differential Scanning Fluorimetry (DSF). DSF profiles of CARD9 and TRIM62ΔRING (labeled as TRIM62ΔR) are presented in the presence or absence of the compounds of the present invention. DMSO was used as a neutral control.
Figure 2B:
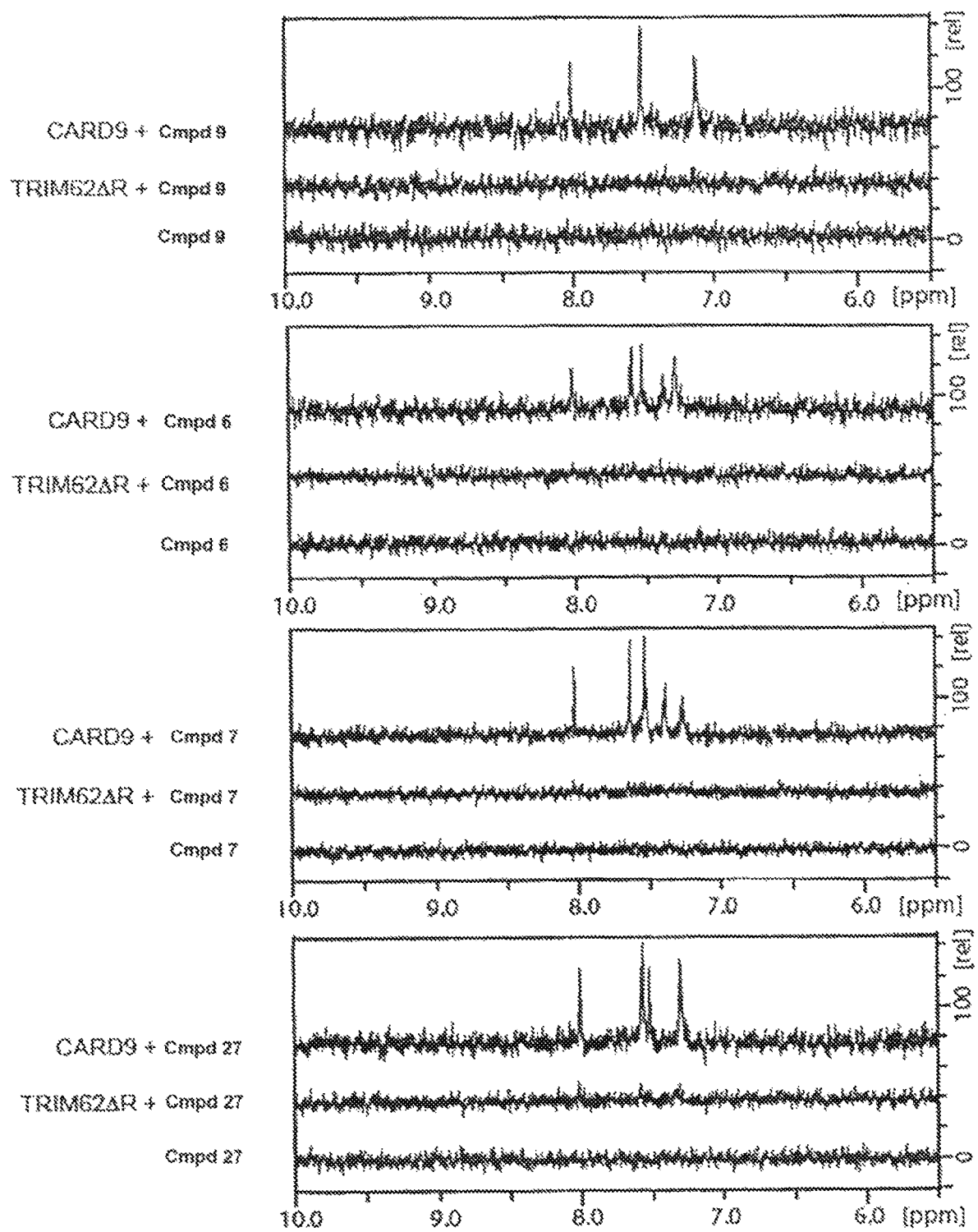
FIG. 2B shows that Saturation Transfer Difference (STD) NMR assays also indicate preferential binding to CARD9. The spectra are for CARD9-compound binding, TRIM62ΔRING-compound binding and compound alone mixtures, respectively.
Figure 2C:
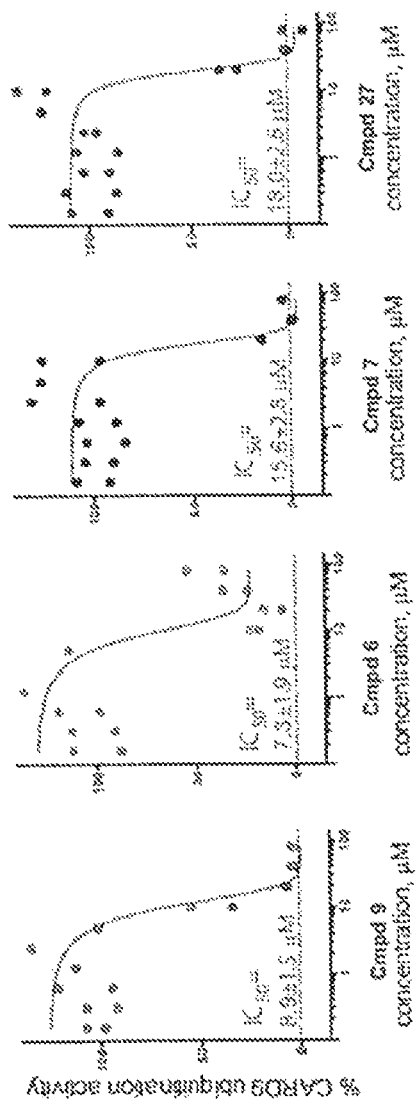
FIG. 2C illustrates how compounds 6, 7, 9, and 27 inhibit the functional ubiquitinylation of CARD9 by TRIM62 in vitro, as measured by the AlphaLISA assay designed to detect polyubiquitinylation of CARD9 in the presence of reconstituted E1-E2-E3 TRIM62 complex.
Figure 2C:
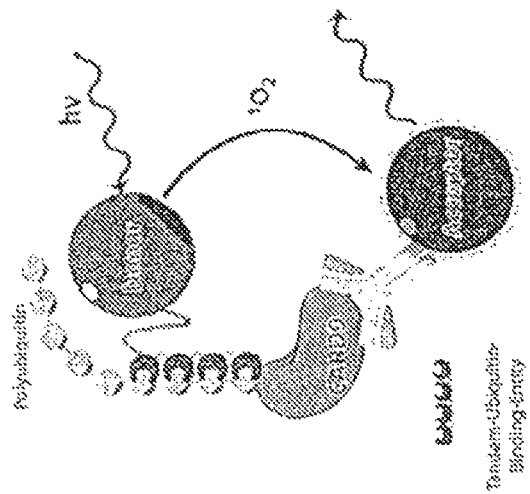
Figure 2D:
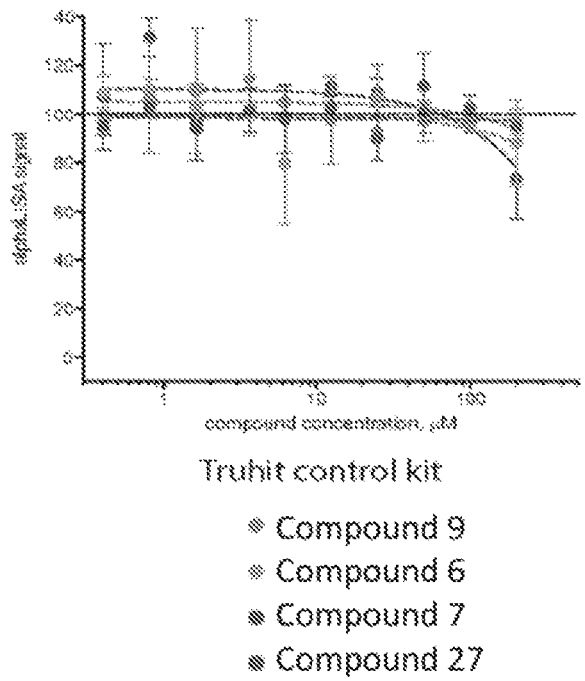
FIG. 2D shows the results of the Truhit alphaLISA assay on compounds 9, 6, 7, and 27 to detect non-specific alphaLISA inhibitors.
Figure 2E:
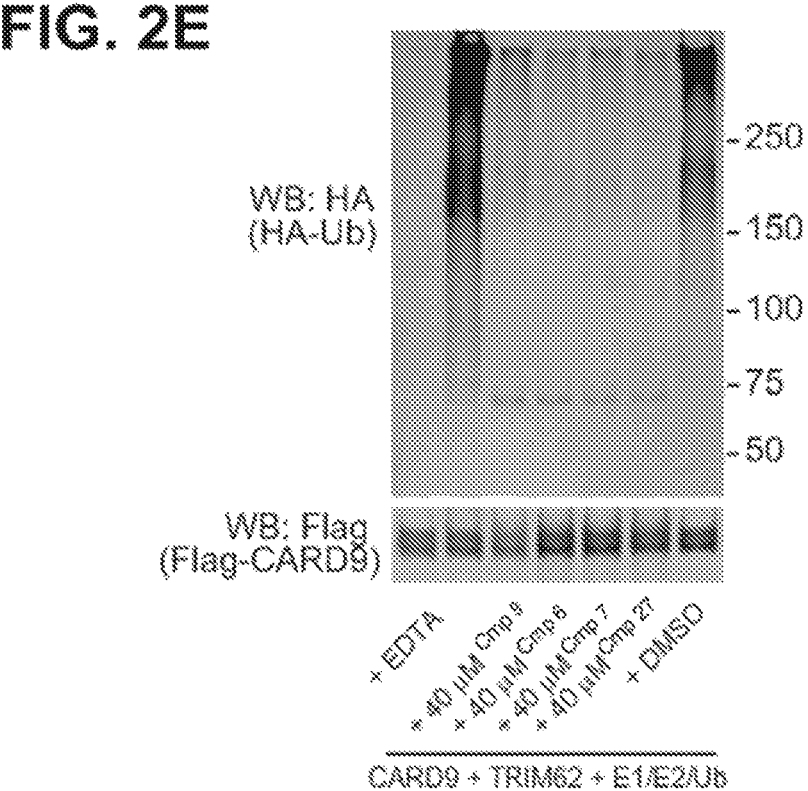
FIG. 2E shows the results of western blotting to detect inhibition of the in vitro CARD9 ubiquitinylation reaction by compounds 9, 6, 7, and 27.

FIG. 2C illustrates how compounds 6, 7, 9, and 27 inhibit the functional ubiquitinylation of CARD9 by TRIM62 in vitro, as measured by the AlphaLISA assay designed to detect polyubiquitinylation of CARD9 in the presence of reconstituted E1-E2-E3 TRIM62 complex. In addition, FIG. 2D shows the results of the Truhit alphaLISA assay on compounds 9, 6, 7, and 27; this assay is designed for the detection of non-specific alphaLISA inhibitors. Data are expressed as mean of percent AlphaLISA signal (100%=mean AlphaLISA signal with DMSO control)+/−s.d. Nonspecific inhibition was not observed. The alphaLISA findings were further corroborated by TRIM62-mediated ubiquitinylation assay coupled with Western blot detection (FIG. 2E). Western blotting detects the inhibition of in vitro CARD9 ubiquitinylation reaction by the compounds.

Figure 4:
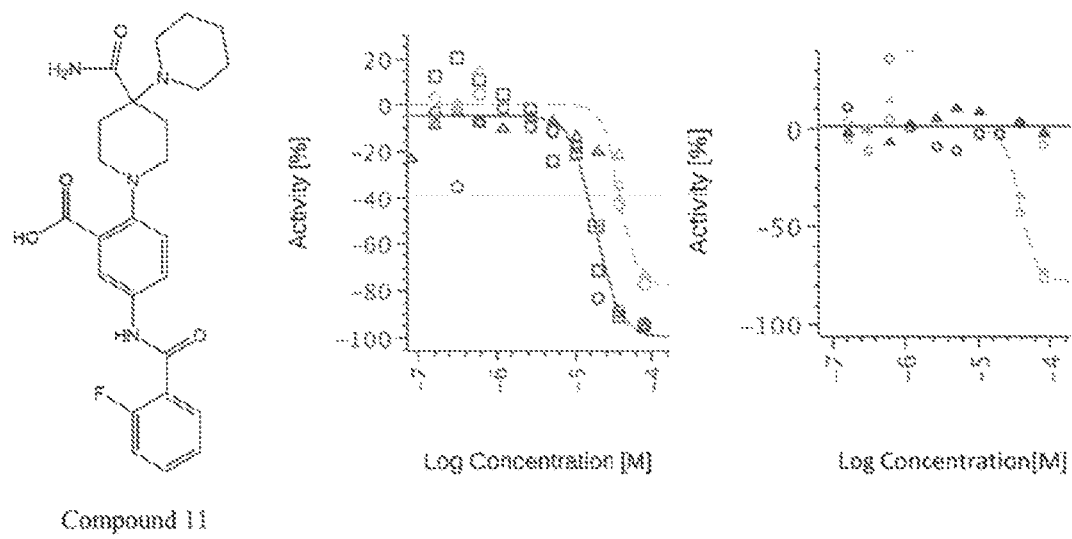
FIG. 4 shows compound 11 is a potent inhibitor of CARD9 in both the Luminex and AlphaLISA ubiquitinylation assays.
Figure 5:
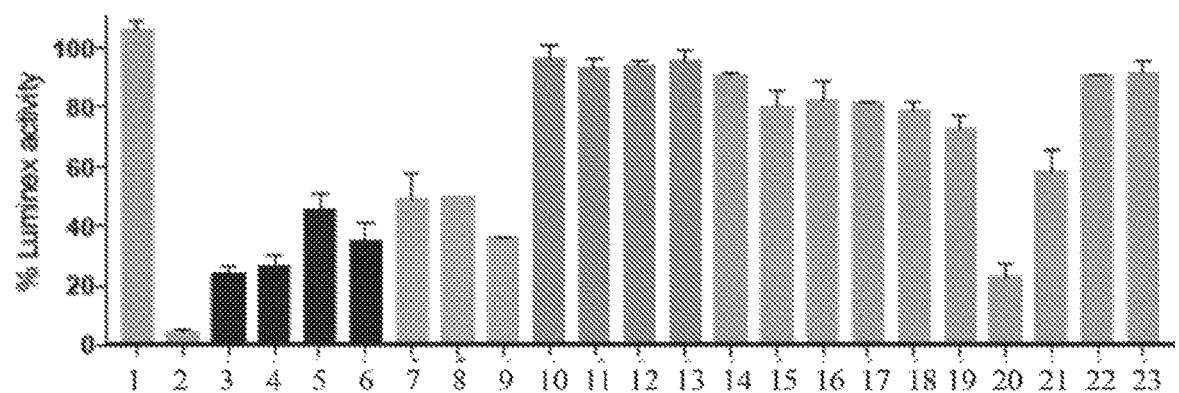
FIG. 5 indicates the % Luminex activity of compounds of the invention, indicating their ability to inhibit the interaction of CARD9 and TRIM62.

FIG. 4 shows compound 11 is a potent inhibitor of CARD9 in both the Luminex and AlphaLISA ubiquitinylation assays. FIG. 5 indicates the % Luminex activity of compounds of the invention, indicating their ability to inhibit the interaction of CARD9 and TRIM62. FIG. 6 provides data for compounds of the invention in both the Luminex and AlphaLISA ubiquitinylation assays, demonstrating their ability to inhibit the interaction of CARD9 and TRIM62 and prevent CARD9 ubiquitinylation.

Example 2

Differential Scanning Calorimetry and STD NMR Assay

FIG. 2A illustrates that certain compounds of the invention directly bind CARD9, but not TRIM62, as evidenced by thermal shift using Differential Scanning Fluorimetry (DSF). DSF profiles of CARD9 and TRIM62ΔRING (labeled as TRIM62ΔR) are presented in the presence or absence of the compounds of the present invention. DMSO was used as a neutral control.

Saturation Transfer Difference (STD) NMR assays (FIG. 2B) also indicate preferential binding to CARD9. The spectra are for CARD9-compound binding, TRIM62ΔRING-compound binding and compound alone mixtures, respectively.

Example 3

Phospho-IKK FACS Assay

Figure 3A:
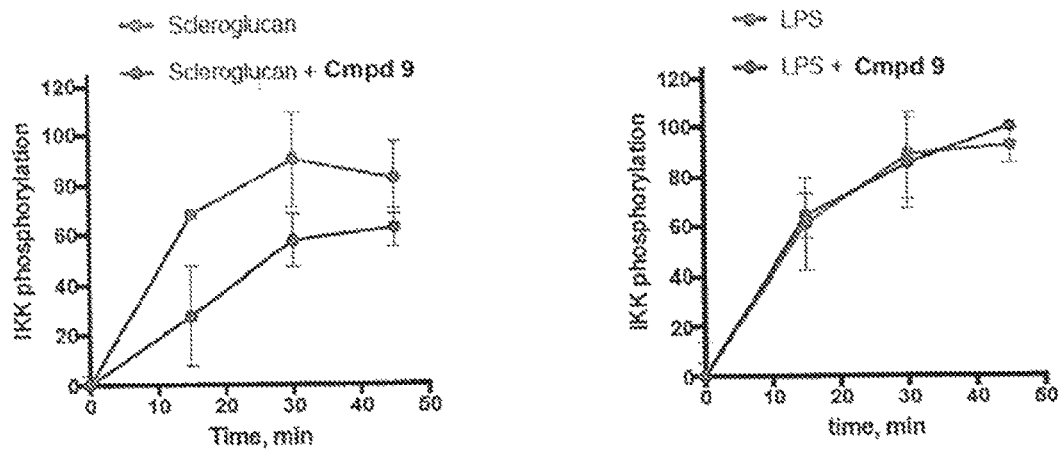
FIG. 3A shows phosphorylation of IKK in the primary bone marrow-derived dendritic cells as assessed in the presence or absence of stimuli (Dectin-1: scleroglucan; TLR4 control: LPS) with compound 9 by fixed cells staining and flow cytometry. CARD9 KO BMDCs were used as a genetic control.
Figure 3B:
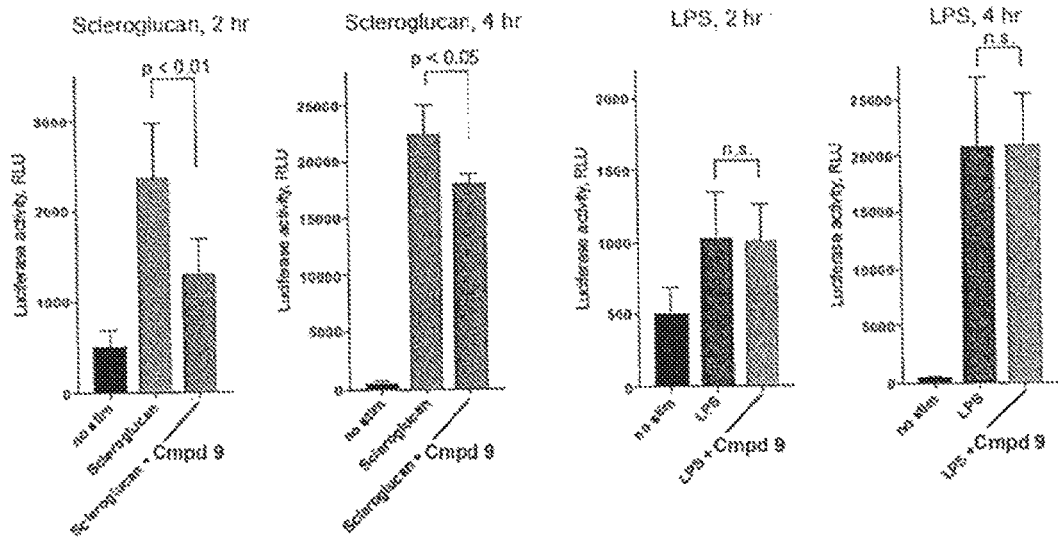
FIG. 3B shows NF-κB activation in THP-1 cells reconstituted with Dectin-1 and NF-κB promoter driven luciferase reporter as measured at 2 hr and 4 hr time points, with scleroglucan (left two plots) and LPS (right two plots) stimuli and presence or absence of compound 9.

In FIGS. 3A-3B, compound 9 attenuates CARD9 signaling in stimulus-dependent manner. FIG. 3A shows phosphorylation of IKK in the primary bone marrow-derived dendritic cells. Cells were treated with the indicated stimuli (Dectin-1, scleroglucan; TLR4 control, LPS) in the presence or absence of 200 μM compound 9 by fixed cells staining and flow cytometry. CARD9 KO BMDCs were used as a genetic control. FIG. 3B shows NF-κB activation in THP-1 cells reconstituted with Dectin-1 and NF-κB promoter driven luciferase reporter as measured at 2 hr and 4 hr time points, with scleroglucan (left two plots) and LPS (right two plots) stimuli and presence or absence of compound 9.

Figure 3C:
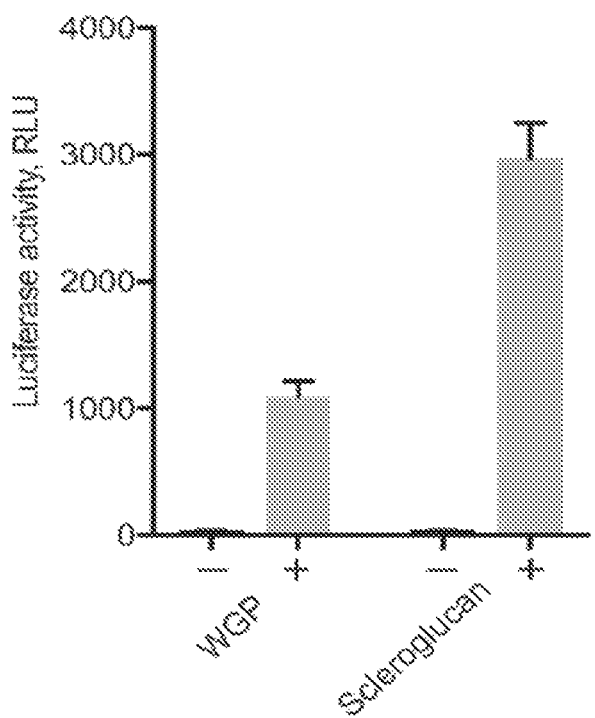
FIG. 3C shows NF-κB activation in THP-1 cells reconstituted with Dectin-1 as measured by NF-κB-driven luciferase reporter in the presence or absence of 50 µg/mL whole glucan protein (WGP) or scleroglucan.
Figure 3D:
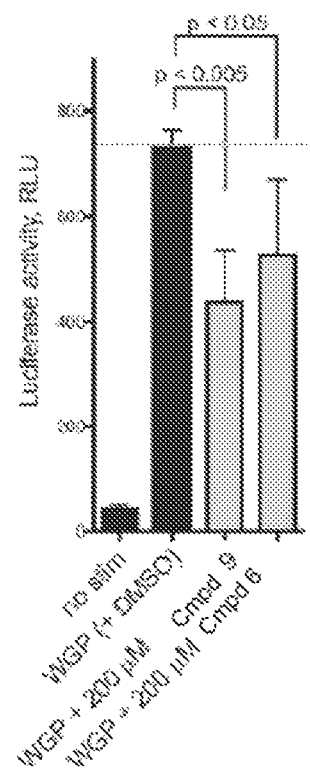
FIG. 3D shows stimulation of cells with WGP in the presence or absence of 9 or 6.
Figure 3E:
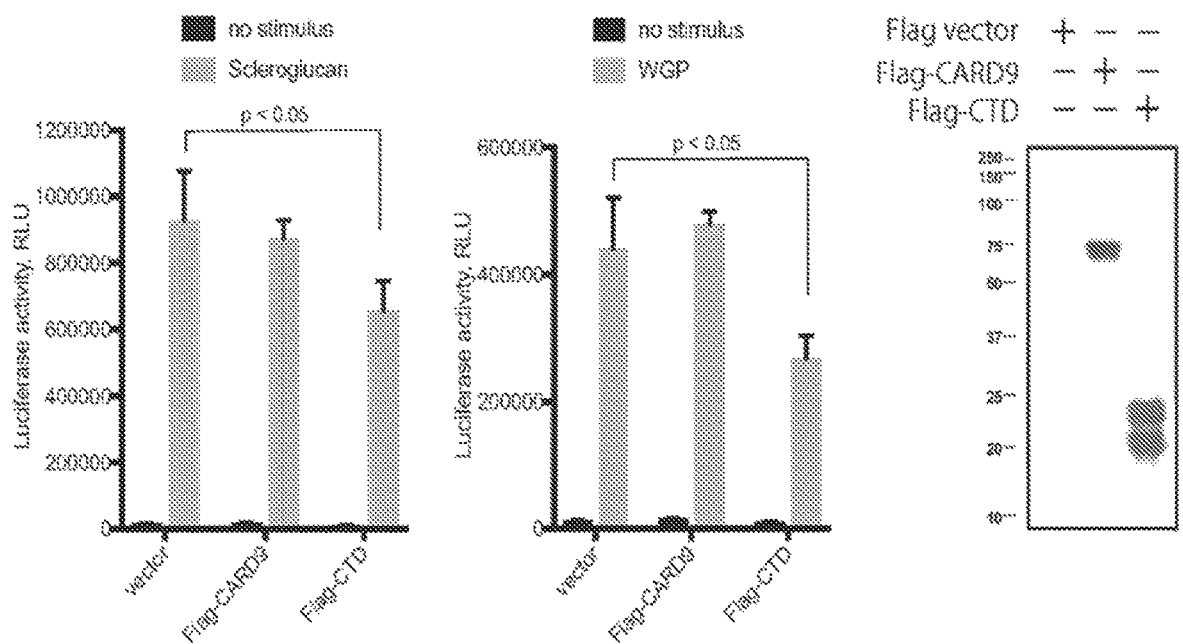
FIG. 3E shows inhibition of Dectin-1-mediated NF-κB luciferase reporter inhibition by heterologous expression of CTD of CARD9 in wild-type THP-1 cells.

In FIGS. 3C-3E, WGP Dectin-1-mediated signaling to NF-κB is inhibited by the CARD9-targeting compounds. FIG. 3C shows that scleroglucan is a more potent ligand than WGP that activates Dectin-1-mediated signaling. NF-κB activation in THP-1 cells reconstituted with Dectin-1 was measured by NF-κB-driven luciferase reporter in the presence or absence of 50 μg/mL WGP or scleroglucan. In FIG. 3D, cells were stimulated with WGP (50 μg/mL) in the presence or absence of 200 μM 9 or 6. At the 4-h time point, luciferase activity was quantified. RLU, relative light units. For FIGS. 3C and 3D, data represent the mean±SD of at least six replicates and are representative of two independent experiments. P values were calculated by Student's t test. In FIG. 3E, inhibition of Dectin-1-mediated (scleroglucan or WGP stimulated) NF-κB luciferase reporter inhibition by heterologous expression of CTD of CARD9 in wild-type THP-1 cells. Flag-vector plasmid or Flag-CARD9 were used as negative controls, and CTD expression was confirmed by anti-Flag Western blot. Data represent mean±SD of three replicates and are representative of two independent experiments.

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

We claim:
1. A method of treating inflammatory bowel disease, comprising administering to a subject a compound of Formula I or a pharmaceutically acceptable salt thereof:

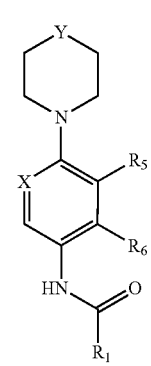

wherein:
X is N or CH;
Y is NR$_2$ or CR$_3$R$_4$;
R$_1$ is selected from alkyl, cycloalkyl, aryl and heteroaryl;
R$_2$ is selected from acyl, aryl, and heteroaryl;
R$_3$ is selected from ethyl and heterocyclyl;
R$_4$ is selected from H, alkyl and amido; and
one of R$_5$ and R$_6$ is —COOH and the other is H.

2. The method of claim 1, wherein the inflammatory bowel disease is selected from Crohn's disease, ulcerative colitis, microscopic colitis, collagenous colitis, lymphocytic colitis, diversion colitis, Behcet's disease and indeterminate colitis.

3. The method of claim 1, wherein the inflammatory bowel disease is Crohn's disease or ulcerative colitis.

4. A method of modulating CARDS, comprising administering to a subject a compound of Formula I or a pharmaceutically acceptable salt thereof:

I wherein:
X is N or CH;
Y is $NR_2$ or $CR_3R_4$;
$R_1$ is selected from alkyl, cycloalkyl, aryl and heteroaryl;
$R_2$ is selected from acyl, aryl, and heteroaryl;
$R_3$ is selected from ethyl and heterocyclyl;
$R_4$ is selected from H, alkyl and amido; and
one of $R_5$ and $R_6$ is —COOH and the other is H.

5. The method of claim 4, wherein modulating CARD9 comprises increasing the activity of a protective variant of CARD9.

6. The method of claim 4, wherein modulating CARD9 comprises decreasing the activity of a risk variant of CARD9.

7. The method of claim 4, wherein X is N.

8. The method of claim 4, wherein X is CH.

9. The method of claim 4, wherein Y is $NR_2$.

10. The method of claim 4, wherein Y is $CR_3R_4$.

11. The method of claim 4, wherein Ri is selected from methyl, butyl, cyclopropyl, phenyl, and thiophenyl.

12. The method of claim 11, wherein $R_1$ is phenyl substituted with one or more substituents selected from methyl, fluoro, and chloro.

13. The method of claim 4, wherein Y is $NR_2$ and $R_2$ is selected from —C(O)Me, phenyl and pyridyl.

14. The method of claim 4, wherein Y is $CR_3R_4$ and $R_3$ is selected from ethyl and piperidinyl.

15. The method of claim 14, wherein the ethyl is optionally substituted with piperidinyl or pyrrolidinyl.

16. The method of claim 14, wherein $R_4$ is H or —C(O)$NH_2$.

17. The method of claim 4, wherein Y is $CR_3R_4$, $R_3$ is piperidinyl and $R_4$ is —C(O)$NH_2$.

18. The method of claim 4, wherein $R_5$ is —COOH and $R_6$ is H.

19. The method of claim 4, wherein $R_5$ is H and $R_6$ is —COOH.

20. A method of modulating CARD9, comprising administering to a subject a compound selected from:

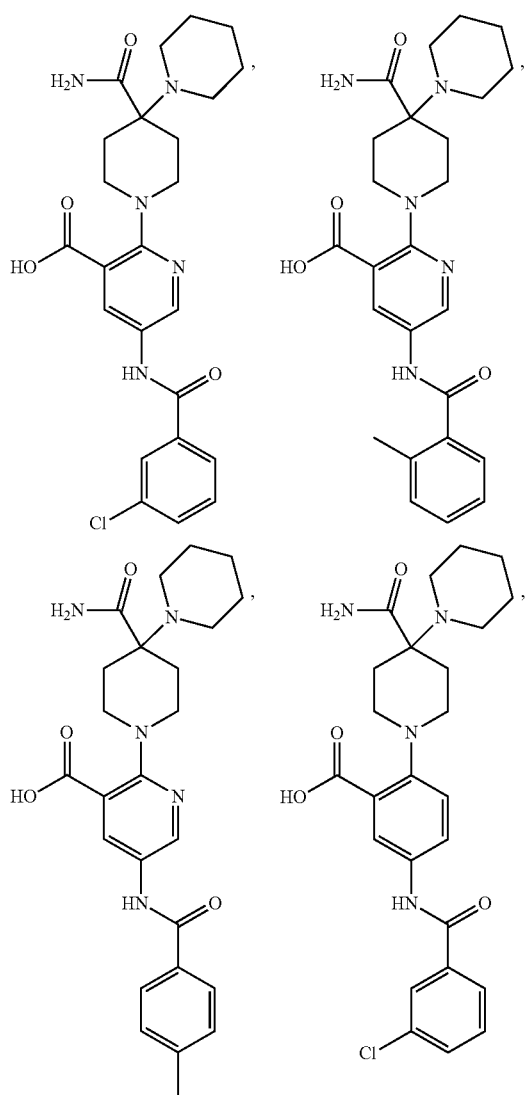
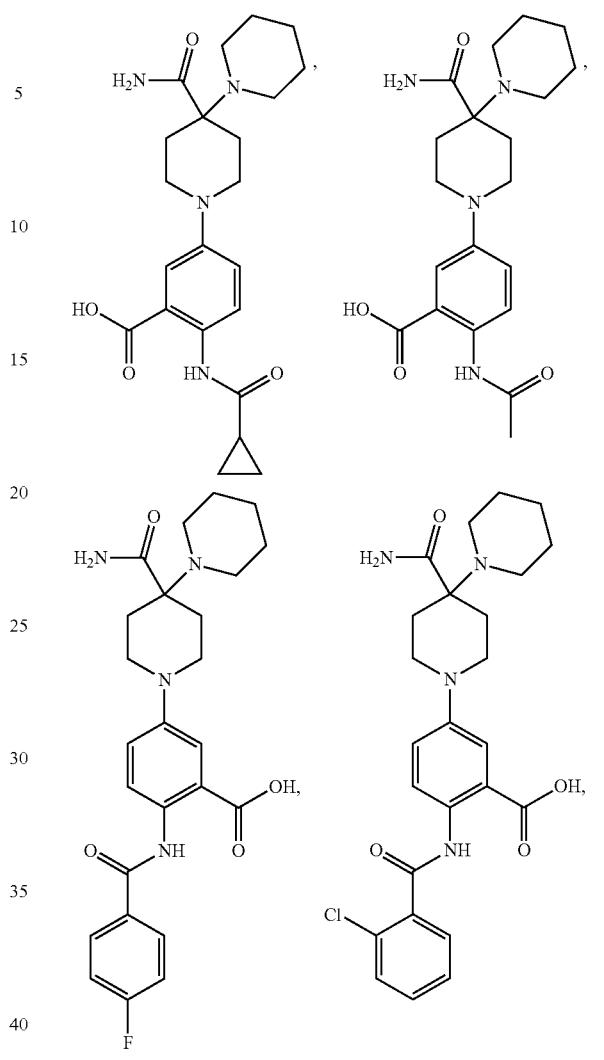
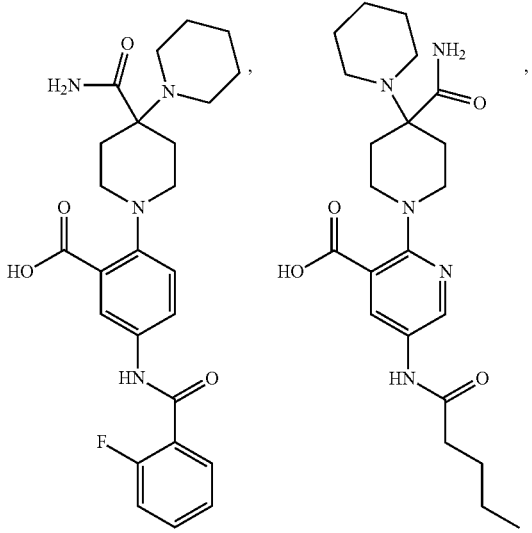
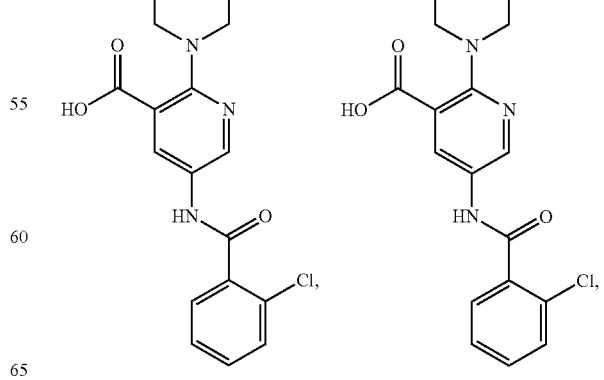

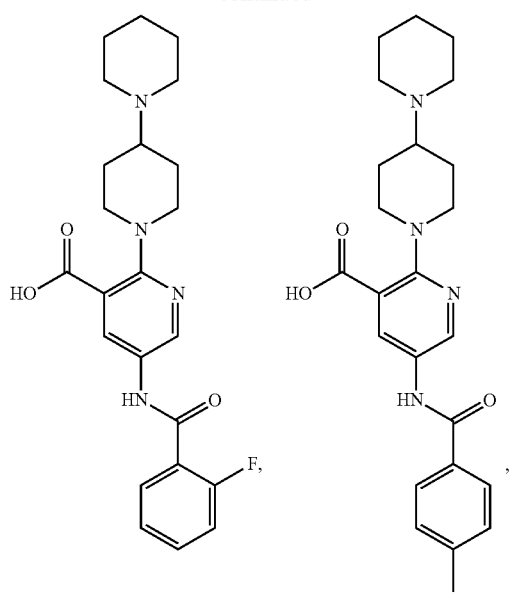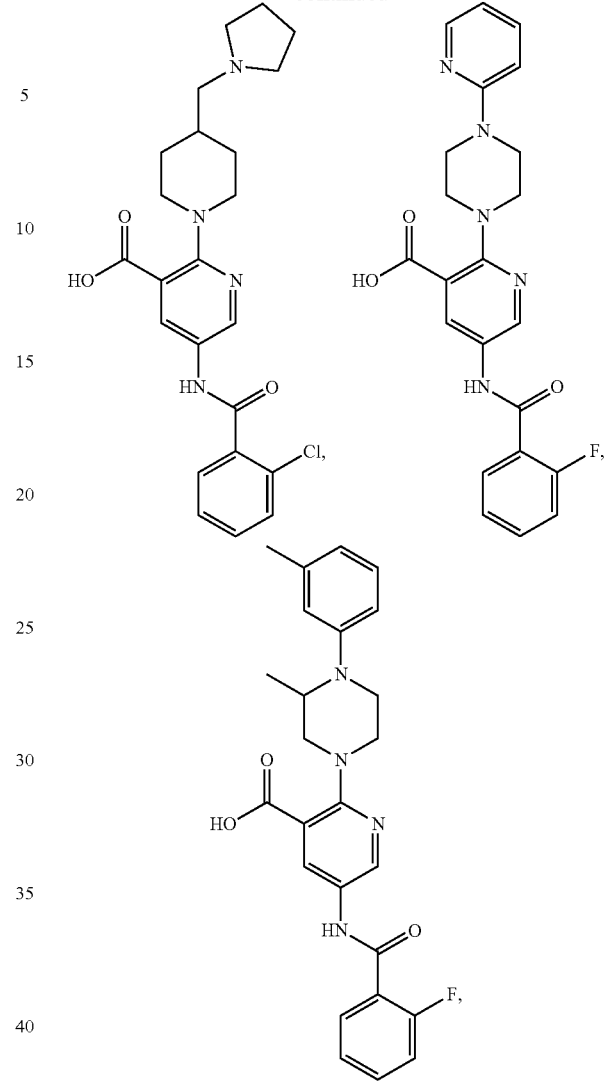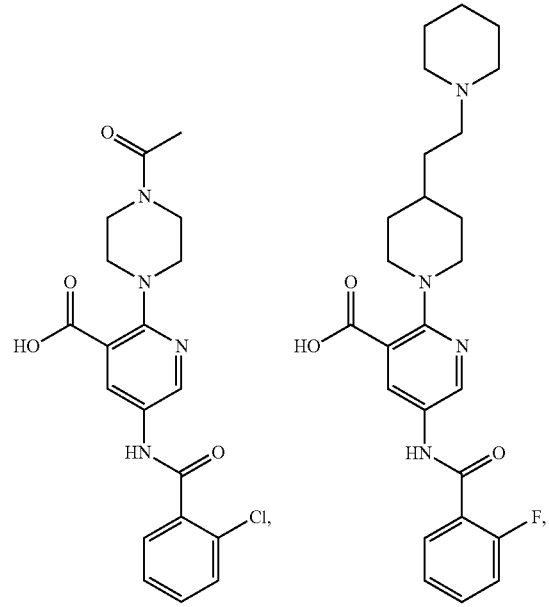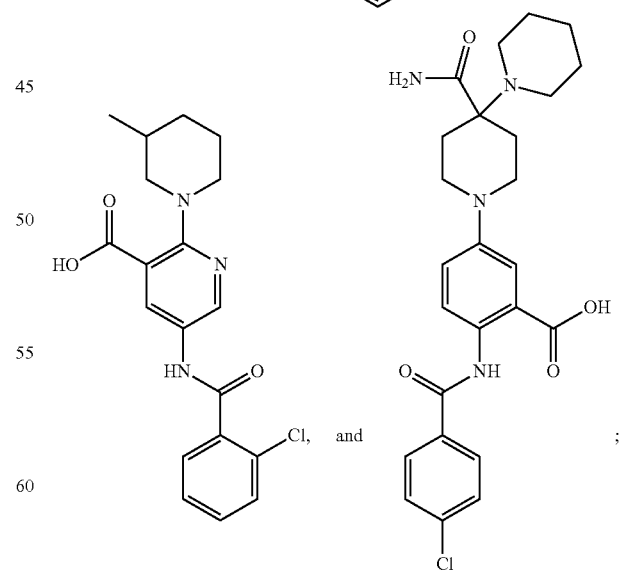
or a pharmaceutically acceptable salt thereof.
* * * * *